United States Patent
Iwata et al.

(10) Patent No.: US 9,980,937 B2
(45) Date of Patent: May 29, 2018

(54) THERAPEUTIC AGENT FOR ALZHEIMER'S DISEASE

(71) Applicant: NAGASAKI UNIVERSITY, Nagasaki-shi, Nagasaki (JP)

(72) Inventors: Nobuhisa Iwata, Nagasaki (JP); Keiro Shirotani, Nagasaki (JP); Masashi Asai, Nagasaki (JP); Takashi Tanaka, Nagasaki (JP)

(73) Assignee: NAGASAKI UNIVERSITY, Nagasaki (JP)

( * ) Notice: Subject to any disclaimer, the term of this patent is extended or adjusted under 35 U.S.C. 154(b) by 0 days. days.

(21) Appl. No.: 15/460,846

(22) Filed: Mar. 16, 2017

(65) Prior Publication Data

US 2017/0252318 A1  Sep. 7, 2017

Related U.S. Application Data

(63) Continuation of application No. PCT/JP2015/081417, filed on Nov. 6, 2015.

(30) Foreign Application Priority Data

Nov. 6, 2014  (JP) .................. 2014-226236
Oct. 1, 2015  (JP) .................. 2015-196282

(51) Int. Cl.
*A61K 31/35* (2006.01)
*A61K 31/352* (2006.01)
*A61K 31/353* (2006.01)

(52) U.S. Cl.
CPC .......... *A61K 31/352* (2013.01); *A61K 31/353* (2013.01)

(58) Field of Classification Search
CPC .................................... A61K 31/35
USPC ................................ 514/453, 456
See application file for complete search history.

(56) References Cited

U.S. PATENT DOCUMENTS

| | | |
|---|---|---|
| 2002/0040052 A1 | 4/2002 | Ito et al. |
| 2008/0227829 A1 | 9/2008 | Hammerstone et al. |
| 2010/0048731 A1 | 2/2010 | Luu et al. |
| 2010/0222423 A1 | 9/2010 | Frank et al. |
| 2011/0111072 A1 | 5/2011 | Pasinetti et al. |
| 2011/0159122 A1 | 6/2011 | Frank |
| 2015/0306122 A1 | 10/2015 | John et al. |

FOREIGN PATENT DOCUMENTS

| | | |
|---|---|---|
| JP | 2007-145839 A | 6/2007 |
| JP | 2007-230878 A | 9/2007 |
| JP | 2007-269650 A | 10/2007 |
| JP | 2010-100540 A | 5/2010 |
| JP | 2013-043863 A | 3/2013 |
| JP | 2013-053133 A | 3/2013 |
| WO | WO 2013/142370 A1 | 9/2013 |
| WO | WO 2013/191236 A | 12/2013 |

OTHER PUBLICATIONS

Ayoub et al., *J. Pharm. Pharmacol.*, 58(4): 495-501 (2006).
Fudouji et al., *J. Agric. Food Chem.*, 57(14): 6417-6424 (2009).
Gauci et al., *J. Alzheimers Dis.*, 27(4): 767-779 (2011).
Iwata et al., *Nat. Med.*, 6(2): 143-150 (2000).
Iwata et al., *Science*, 292(5521): 1550-1552 (2001).
Kang et al., *Bioorg. Med. Chem. Lett.*, 15(15): 3588-3591 (2005).
Kim et al., *J. Neurochem.*, 112(6): 1415-1430 (2010).
Kiss et al., *Pharmazie*, 61(1): 66-69 (2006).
Lim et al., *J. Nutr. Biochem.*, 24(7): 1302-1313 (2013).
Mandel et al., *CNS Neurosci. Ther.*, 14(4): 352-365 (2008).
Mecocci et al., *Front. Pharmacol.*, 5: 147 (2014).
Melzig et al., *Pharmazie*, 57(8): 556-558 (2002).
Melzig et al., *Phytomedicine*, 10(6-7): 494-498 (2003).
Murakami et al., "Examination of prevention effect of Alzheimer's disease by the tea catechins," *Life Support*, 18: 117, Supplement (2006) [available on the internet at http://doi.org/10.5136/lifesupport.18.Supplement_117].
Shizuoka-Ken Economy and Industry Department Agricultural Production Division, "Health Benefits of Green Tea-Navigation to Functional and Mechanistic Aspects 2013," pp. 51-52 (2013) [available on the internet at http://www.pref.shizuoka.jp/sangyou/sa-340/documents/mechanism2013.pdf].
Thapa et al., *Biochemistry*, 50(13): 2445-2455 (2011).
Zhao et al., *Molecules*, 18(8): 9949-9965 (2013).
Japanese Patent Office, International Preliminary Report on Patentability in International Patent Application No. PCT/JP2015/081417 (Aug. 5, 2016).
Japanese Patent Office, International Search Report in International Patent Application No. PCT/JP2015/081417 (Jan. 12, 2016).

*Primary Examiner* — Raymond J Henley, III
(74) *Attorney, Agent, or Firm* — Leydig, Voit & Mayer, Ltd.

(57) ABSTRACT

The present invention aims to provide a pharmaceutical agent for the prophylaxis and/or treatment of Alzheimer's disease, which has a novel action mechanism and shows less side effects. A polyphenol derivative having liposolubility enhanced by the introduction of at least one kind of a liposoluble group selected from the group consisting of a chain saturated hydrocarbon group, a chain unsaturated hydrocarbon group, a cyclic saturated hydrocarbon group, a cyclic unsaturated hydrocarbon group, an aromatic hydrocarbon group, a liposoluble vitamin residue and a sterol residue has an action to potentiate neprilysin activity, and is useful as a pharmaceutical agent for the prophylaxis and/or treatment of Alzheimer's disease.

20 Claims, 8 Drawing Sheets

P<0.05, significantly different from control

*P<0.05, significantly different from control

Fig. 5

| | Log P octanol | Total NEP act | NEP protein | NEP mRNA | Cell surface NEP act | APPsα | APPsβ | APPα/ APPβ | BACE1 protein | BACE1 mRNA | ADAM10 protein | ADAM9 mRNA | ADAM10 mRNA | ADAM17 mRNA |
|---|---|---|---|---|---|---|---|---|---|---|---|---|---|---|
| NUP-18 | -ᵃ | ←← | ← | | ←← | ← | ←← | ← | | | | | | |
| NUP-16 | 2.55 | ↑↑ | ← | ←← | ←← | ←← | ↑ | ← | | | | | | ←← |
| NUP-11 | >10 | ←← | ←← | ←← | ←← | ↑ | ←← | ←← | → | → | | | | ← |
| NUP-19 | >10 | ←← | ← | | ←→ | ↑ | ←← | ←← | | | | | | ← |
| NUP-6 | 1.85 | ← | ↑ | | ←← | ↑ | ← | → | → | | | | | |
| EGCg | 1.0 | ↑ | ↑ | | ←← | → | ← | → | | | | | | |
| NUP-15 | -ᵃ | ↑ | ↑ | | ↑ | → | ↑ | ↑ | | | ← | | | |
| NUP-E15-1 | -ᵃ | ←← | ← | ←← | ↑ | | ←← | ←← | ←← | → | | ← | | ←← |
| NUP-E15-2 | -ᵃ | ← | | ← | ↑ | | ←← | ←← | ← | → | | | | ← | a, unanalyzed

*p < 0.05, significantly different from control (DMSO)
p < 0.05, significantly different from cocktail

THERAPEUTIC AGENT FOR ALZHEIMER'S DISEASE

CROSS-REFERENCE TO RELATED APPLICATIONS

This patent application is a continuation of International Patent Application No. PCT/JP2015/081417, filed Nov. 6, 2015, which claims the benefit of Japanese Patent Application No. 2014-226236, filed on Nov. 6, 2014, and Japanese Patent Application No. 2015-196282, filed on Oct. 1, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 242,371 bytes ASCII (Text) file named "728212SequenceListing.txt," created Mar. 15, 2017.

TECHNICAL FIELD

The present invention relates to a novel therapeutic drug for Alzheimer's disease (AD), which is different from the conventional therapeutic drugs in the action mechanism. In more detail, the present invention relates to a pharmaceutical agent for the prophylaxis and/or treatment of AD, which is based on an action to potentiate the activity of neprilysin which is a peptidase responsible for the degradation system of amyloid-β peptide (Aβ) and/or an action to potentiate the activity of α-secretase which contributes to the inhibition of Aβ production.

BACKGROUND ART

AD is a progressive neurodegenerative disease which is the main factor of senile dementia, and the pathological cascade before appearance of clinical symptoms includes accumulation of extracellular Aβ→aggregation and accumulation of intracellular tau→neurodegeneration and neuronal death (the amyloid hypothesis). Therefore, AD is considered to begin with the accumulation of Aβ, and the fundamental treatment thereof requires removal of Aβ from the brain by inhibiting Aβ production, promoting degradation, suppressing aggregation, and removing aggregate deposit. Studies are being conducted competitively on a global scale for the development of such anti-Aβ drugs.

As a therapeutic drug for AD, some pharmaceutical agents such as Aricept (donepezil) and the like exist. However, they only have an effect of alleviating the disease state, and are not a fundamental therapeutic agent nor disease-modifying drug. On the other hand, in the research of Aβ metabolism, analysis of β- and γ-secretases related to the production system was conventionally performed. Therefore, the development of inhibitors or modulators targeting these enzymes also preceded in the drug discovery research of AD, and clinical trials were conducted for a plurality of pharmaceutical agents. However, the developments have been stopped one after another as the situation stands, due to the problems of side effects and the like. As for removal of aggregate deposit (Aβ vaccine therapy) and aggregation inhibitors, as other action sites, they were advanced to the clinical trial, but the development thereof was forced to be discontinued in every case due to the side effects.

As regards the degradation system of intracerebral Aβ, it has been reported that peptidase called neprilysin is a major enzyme responsible for degradation (non-patent documents 1, 2). Neprilysin is one kind of neutral endopeptidase present in various tissues of animals and is a membrane-bound enzyme having a catalytic site in the extracellular domain. It is known by in vitro experiments that enkephalin, substance P, atrial natriuretic peptide (ANP), gastrin releasing peptide (GRP), endothelin and the like can be a substrate for neprilysin.

The results correlating the progression of Aβ accumulation observed in normal aged brain and amyloid pathology in AD with a decrease in the intracerebral neprilysin level have been reported. The expression level markedly decreases with age in the cerebral cortex and hippocampus of normal mouse and AD model mouse. Recently, it has been revealed that a similar decrease occurs in human as well, and an inverse correlation between a decrease in the neprilysin level and the Aβ42 level of insoluble fraction has been reported.

Same results have also been reported by plural independent research groups on the decrease in the neprilysin levels in the AD brain. It is known that the expression level and the protein amount of neprilysin decrease by nearly 50% in the hippocampus and lateral lobe at pre-stage of AD. In the cerebellum which is resistant to amyloid pathology, the expression level of neprilysin is higher than in hippocampus and lateral lobe, and the expression of neprilysin does not decrease. On the other hand, in the autopsy brain with advanced amyloid pathology, the decrease in the neprilysin level is further strengthened and has been shown to drastically decrease by 70% that of the control group.

AD therapeutic drug focusing on the degradation system is expected to be a fundamental therapeutic drug for AD. At present, however, it is only in the stage of gene therapy of AD using the neprilysin gene being tried using a model mouse.

Polyphenol is well-known to have an antioxidant action, a cholesterol lowering action, an antibacterial action and the like, and thus generally known to exert a favorable influence on health maintenance. There are also reports that catechin, which is a polyphenol as a component derived from tea, is effective for AD (non-patent documents 3-5). It has been reported that (−)-epigallocatechin-3-O-gallate (EGCg), which is one kind of polyphenol and has the following structure

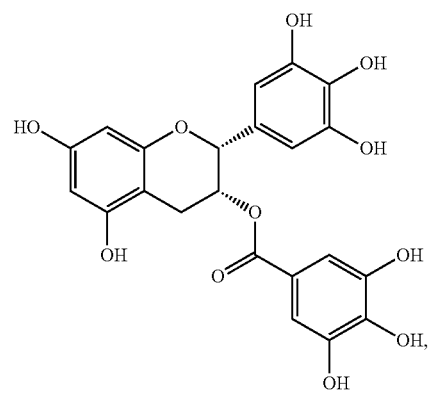 [SMILES: O=C(O[C@@H]1Cc2c(O)cc(O)cc2O[C@@H]1c1cc(O)c(O)c(O)c1)c1cc(O)c(O)c(O)c1]

increases enzyme activity of neutral endopeptidase in nerve system cells (non-patent documents 6-9). Since general artificial substrates of neutral endopeptidase were used in the experiments thereof, it is unknown which enzyme was actually reacted on. Derivatives in which alkyl chain was added to EGCg to increase liposolubility (hydrophobicity) and bioavailability (absorption efficiency in the intestine and intracerebral transferability) have been reported (patent document 1, non-patent document 10). Amentoflavone, which is a polyphenol contained in ginkgo leaf and the like, has been reported to show inhibition of Aβ aggregation and cell death protective effect (non-patent documents 11, 12). Apigenin, which is a polyphenol contained in many plants, has also been reported to show an Aβ aggregation inhibitory effect (non-patent documents 13, 14). Kaempferol contained in strawberry and the like is also known to show inhibition of Aβ production, inhibition of Aβ aggregation, and cell death protective effect.

However, there is no paper showing the relationship between any polyphenol and neprilysin and it is not described or suggested that a more superior anti-AD effect can be obtained by derivatizing the polyphenol.

As enzymes that metabolize amyloid precursor protein (APP), α-, β- and γ-secretases are known. Aβ is produced by β- and γ-secretases, while α-secretase cleaves APP inside Aβ. When APP is metabolized by α-secretase, Aβ is not produced. Therefore, AD therapeutic drugs focusing on the enhancement of α-secretase activity are also expected.

DOCUMENT LIST

Patent Document patent document 1: JP-A-2010-100540

Non-Patent Documents non-patent document 1: Iwata N et al., Nat Med. 2000 6(7):718-719.
non-patent document 2: Iwata N et al., Science. 2001 292(5521):1550-1552.
non-patent document 3: Mandel S A et al., CNS Neurosci Ther. 2008 14(4):352-365.
non-patent document 4: Kim J et al., J Neurochem. 2010 112(6):1415-1430.
non-patent document 5: Mecocci P et al., Front Pharmacol. 2014 5:147.
non-patent document 6: Kiss A et al., Pharmazie. 2006 61:66-69.
non-patent document 7: Melzig M F, Janka M, Phytomedicine. 2003 10:494-498.
non-patent document 8: Melzig M F, Escher F, Pharmazie. 2002 57:556-558.
non-patent document 9: Ayoub S, Melzig M F, J Pharm Pharmacol. 2006 58:495-501.
non-patent document 10: Fudouji R et al., J Agric Food Chem. 2009 57(14):6417-6424.
non-patent document 11: Thapa A, et al., Biochemistry. 2011 50(13):2445-2455.
non-patent document 12: Kang S S, et al., Bioorg Med Chem Lett. 2005 15(15):3588-3591.
non-patent document 13: Zhao L, et al., Molecules. 2013 18(8):9949-9965.
non-patent document 14: Gauci A J, et al., J Alzheimers Dis. 2011 27(4):767-779.

SUMMARY OF THE INVENTION

Problems to be Solved by the Invention

An object of the present invention is to provide a pharmaceutical agent for the prophylaxis and/or treatment of AD, which has a novel action mechanism and shows reduced side effects.

Means of Solving the Problems

In view of the above-mentioned problem, the present inventors have intensively searched for a low-molecular-weight compound that potentiate neprilysin activity, and successfully obtained a compound that strongly upregulates neprilysin activity by increasing liposolubility of originally water-soluble polyphenol. Furthermore, the polyphenol derivative also has an action to potentiate α-secretase activity. These actions have made it possible to reduce intracerebral accumulation of Aβ, which resulted in the completion of the present invention.

The present invention is as shown below.
[1] A pharmaceutical agent for the prophylaxis and/or treatment of AD, which comprises a polyphenol derivative as an active ingredient.
[1-1] A method for the prophylaxis and/or treatment of AD, comprising administering an effective amount of a polyphenol derivative to a patient in need thereof.
[1-2] A polyphenol derivative for use in the prophylaxis and/or treatment of AD.
[2] The pharmaceutical agent of the above-mentioned [1]; the method of the above-mentioned [1-1]; or the derivative of the above-mentioned [1-2], wherein the polyphenol derivative is a liposoluble polyphenol derivative.
[3] The pharmaceutical agent; method; or derivative of the above-mentioned [2], wherein the liposoluble polyphenol derivative is a liposoluble catechin derivative.
[4] The pharmaceutical agent; method; or derivative of the above-mentioned [3], wherein the liposoluble catechin derivative is a compound wherein a liposoluble group is introduced into the EGCg derivative or (−)-epicatechin-3-O-gallate derivative represented by the formula (I):

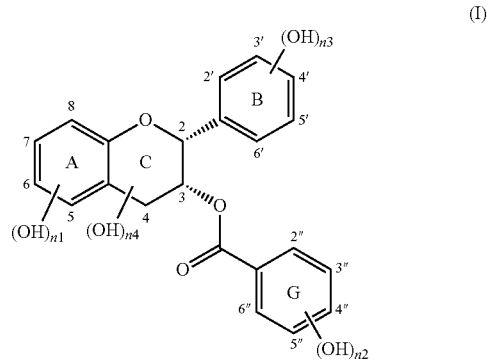

wherein n1 is the number of hydroxyl groups bonded to ring A, and is an integer of 0-4; n2 is the number of hydroxyl groups bonded to ring G, and is an integer of 0-5; n3 is the number of hydroxyl groups bonded to ring B, and is an integer of 0-5; n4 is the number of hydroxyl groups bonded to ring C, and is 0 or 1; and n1+n2+n3+n4 is two or more.
[5] The pharmaceutical agent; method; or derivative of the above-mentioned [3], wherein the liposoluble catechin derivative is a compound wherein a liposoluble group is introduced into the (−)-epigallocatechin derivative or (−)-epicatechin derivative represented by the formula (II):

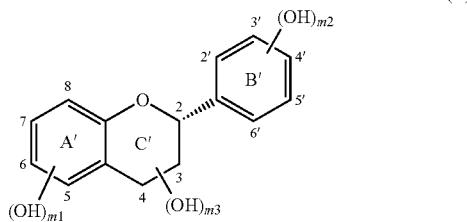

wherein m1 is the number of hydroxyl groups bonded to ring A', and is an integer of 0-4; m2 is the number of hydroxyl groups bonded to ring B', and is an integer of 0-5; m3 is the number of hydroxyl groups bonded to ring C', and is an integer of 0-2; and m1+m2+m3 is two or more.

[6] The pharmaceutical agent; method; or derivative of the above-mentioned [4] or [5], wherein the liposoluble group is selected from the group consisting of a chain hydrocarbon group, a cyclic hydrocarbon group, an aromatic hydrocarbon group, a liposoluble vitamin residue and a sterol residue, each of which optionally has substituent(s).

[7] The pharmaceutical agent; method; or derivative of the above-mentioned [4] or [5], wherein the liposoluble group is a chain hydrocarbon group optionally having substituent(s).

[8] The pharmaceutical agent; method; or derivative of any of the above-mentioned [4]-[7], wherein the liposoluble group is directly introduced into ring A or ring A' via a C—C bond.

[9] The pharmaceutical agent; method; or derivative of any of the above-mentioned [4]-[7], wherein the liposoluble group is introduced without using an S-ester bond or O-ester bond.

[10] The pharmaceutical agent; method; or derivative of any of the above-mentioned [4]-[9], wherein the ring C or ring C' has a carbonyl group at the 4-position.

[11] The pharmaceutical agent; method; or derivative of the above-mentioned [2], wherein the liposoluble polyphenol derivative has a coefficient of partition (log P) of not less than 1.8-fold that of (−)-epigallocatechin-3-O-gallate used as a control.

[12] The pharmaceutical agent of the above-mentioned [1]; the method of the above-mentioned [1-1]; or the derivative of the above-mentioned [1-2], wherein the polyphenol derivative is at least one kind selected from the following compound group:

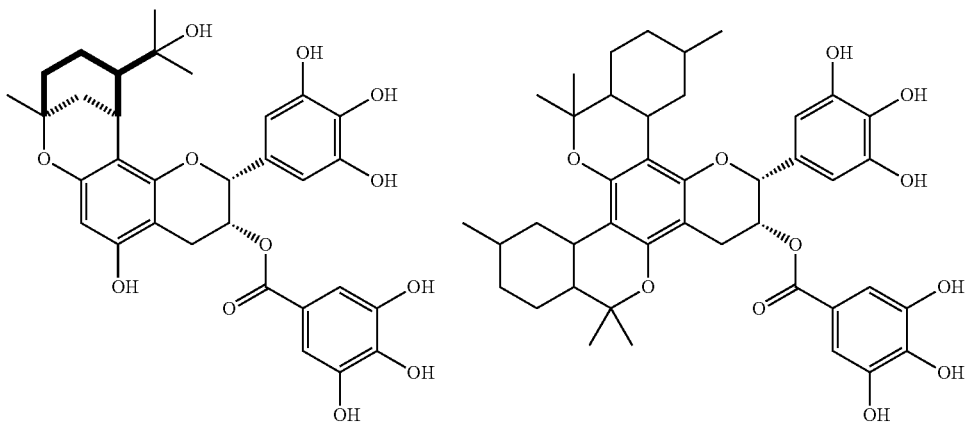

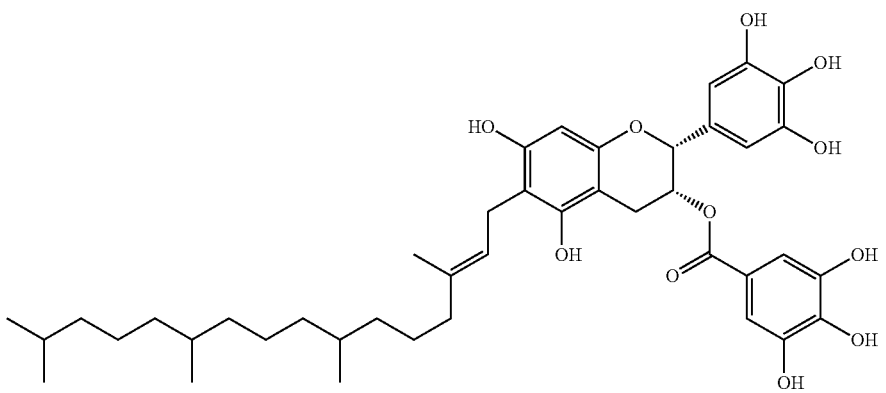

7
8
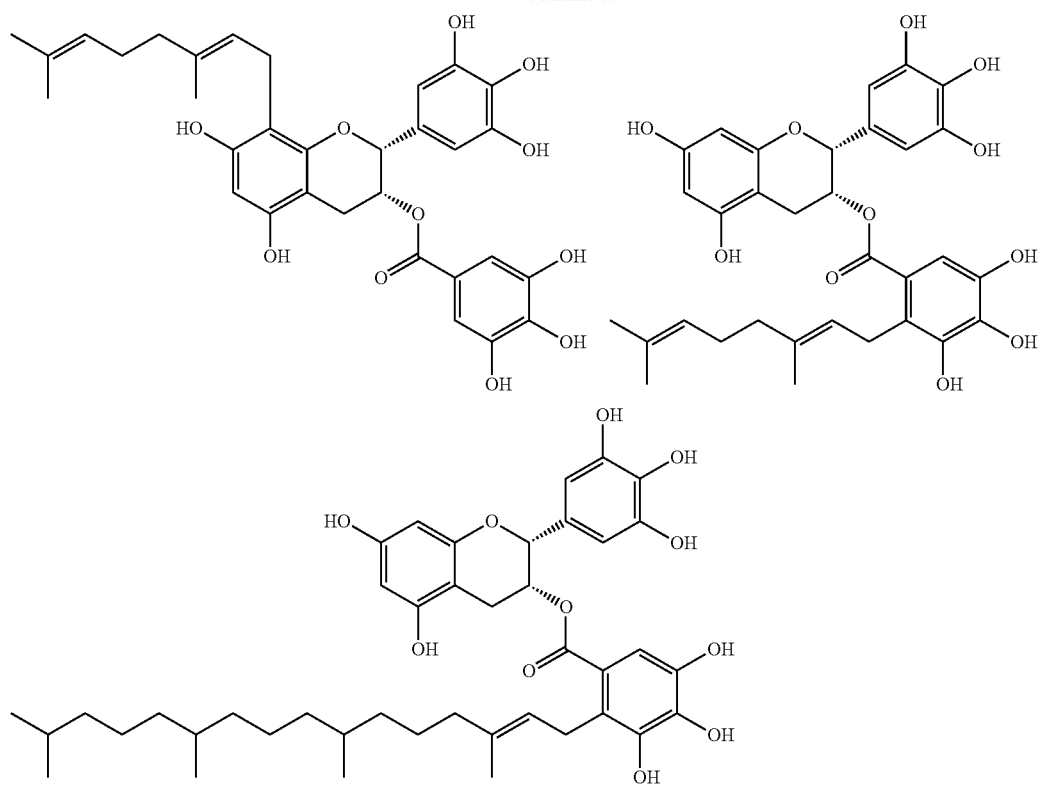
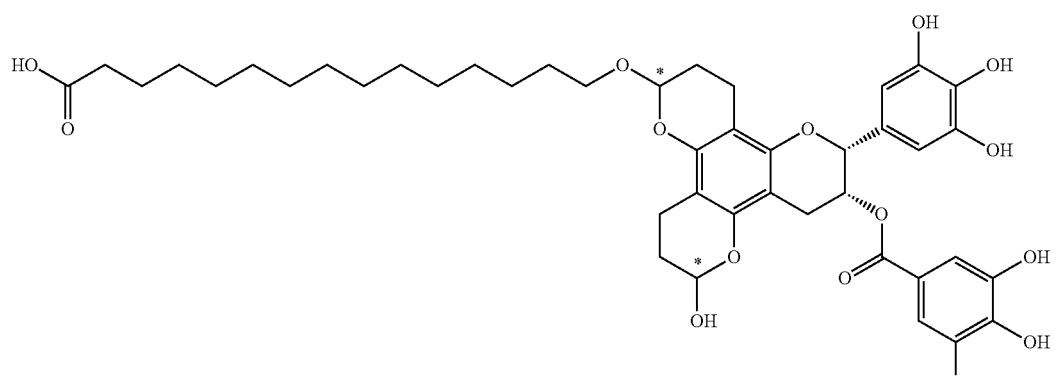
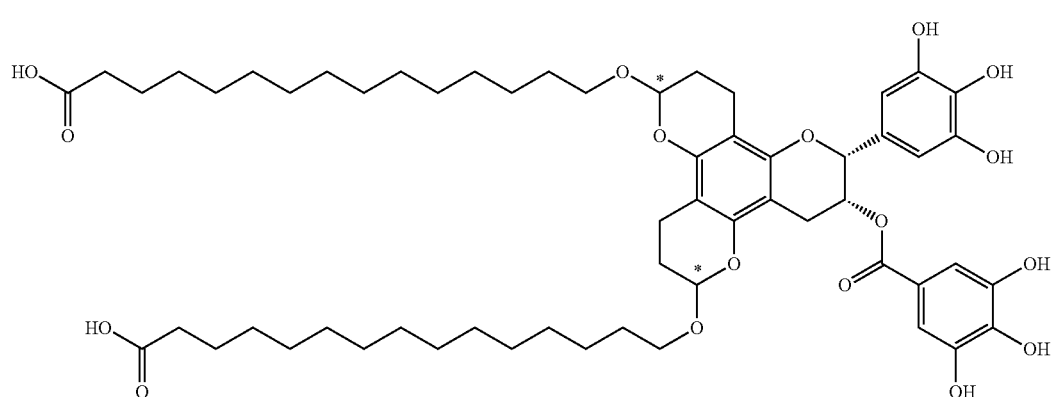

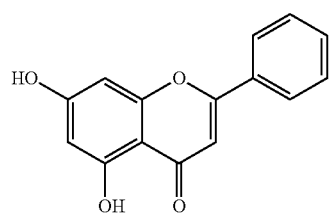
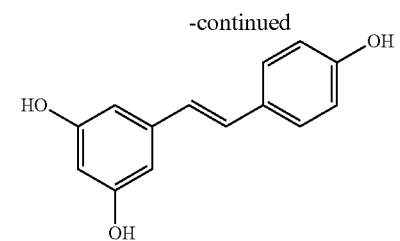
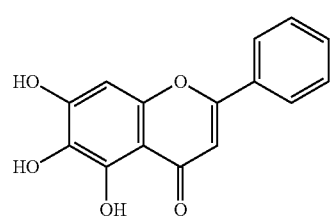
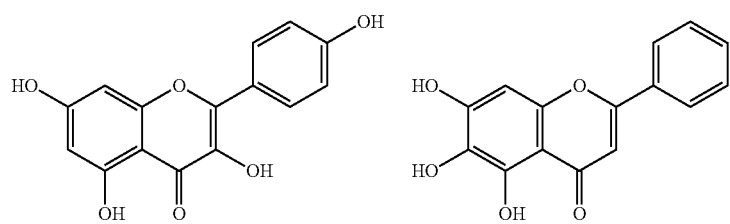
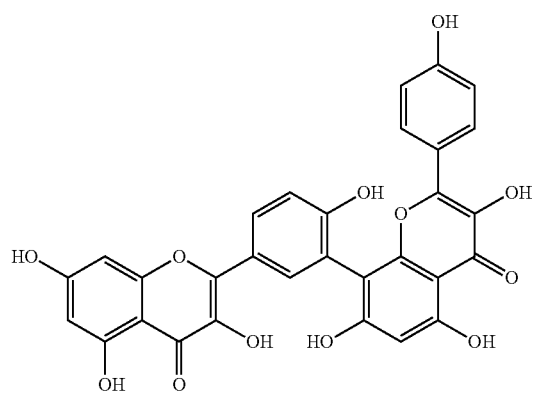
[13] The pharmaceutical agent of the above-mentioned [1]; the method of the above-mentioned [1-1]; or the derivative of the above-mentioned [1-2], wherein the polyphenol derivative is at least one kind selected from the following compound group:
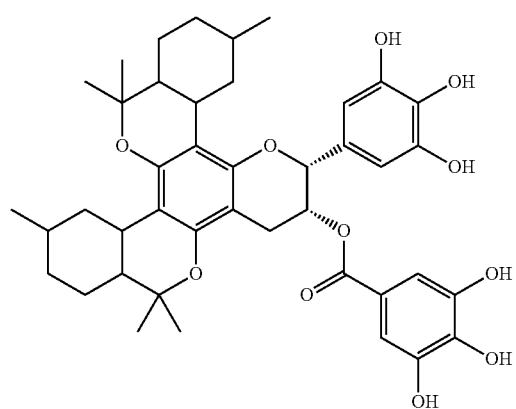

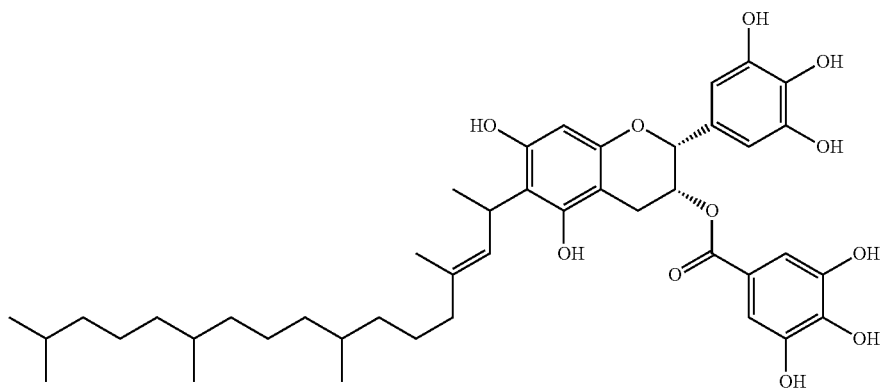
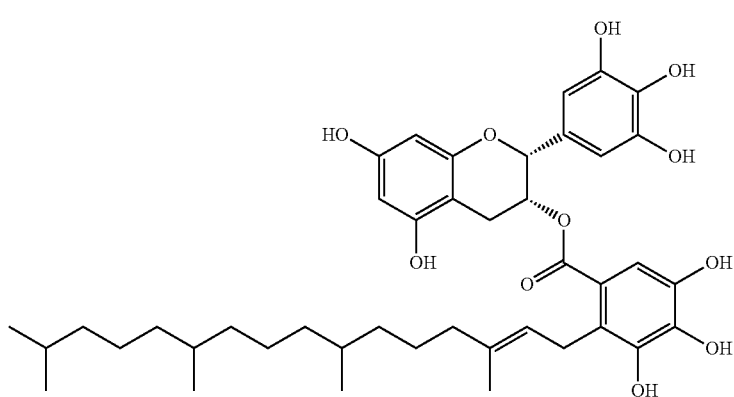
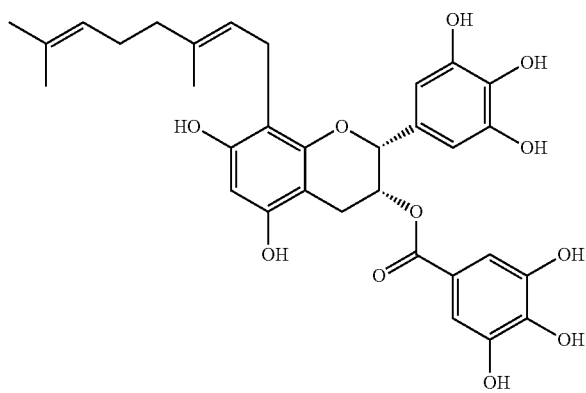
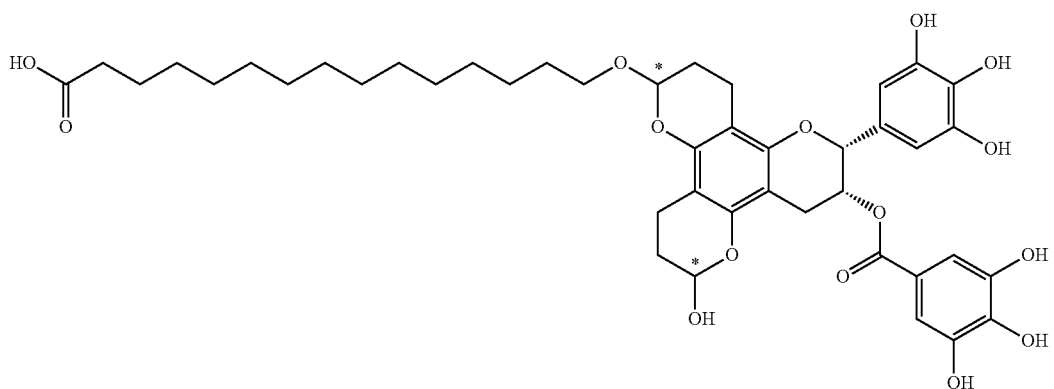

-continued

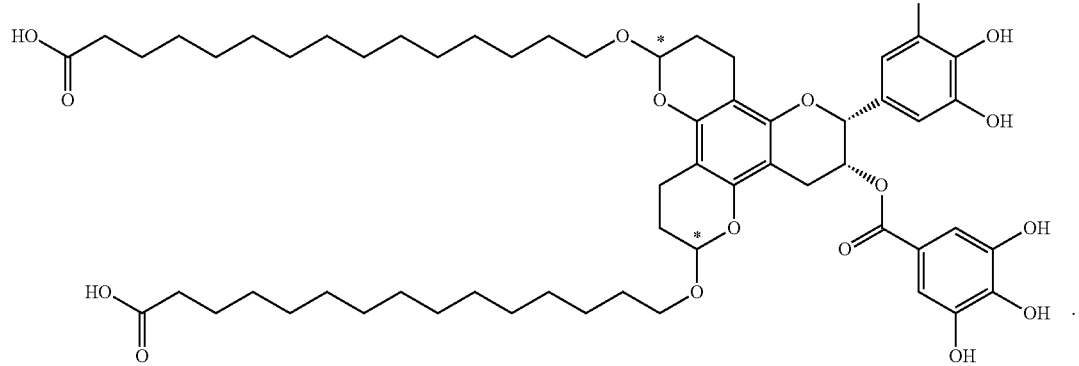

[14] The pharmaceutical agent of the above-mentioned [1]; the method of the above-mentioned [1-1]; or the derivative of the above-mentioned [1-2], wherein the polyphenol derivative is a catechin derivative or a proanthocyanidin derivative produced by reacting (i) catechin or proanthocyanidin, and (ii) a compound represented by the following formula

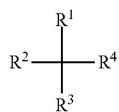

wherein
$R^1$ is a hydrocarbon group;
$R^2$ is hydrogen or hydrocarbon group;
$R^3$ is hydrogen or hydrocarbon group;
$R^4$ is a hydroxyl group, or
$R^3$ and $R^4$ are joined to show a keto group.

[15] The pharmaceutical agent of the above-mentioned [1]; the method of the above-mentioned [1-1]; or the derivative of the above-mentioned [1-2], wherein the polyphenol derivative is a catechin derivative or a proanthocyanidin derivative produced by reacting (i) catechin or proanthocyanidin, and (ii) 2-hexenal, 2-nonenal, cinnamaldehyde, ferulaldehyde, p-coumaraldehyde, citral, citronellal, geranial, geraniol, farnesal, farnesol, 3,7,11,15-tetramethylhexadecenal, phytol, 3-nonen-2-one or perillaldehyde by adding an acid.

[16] The pharmaceutical agent; method; or derivative of any of the above-mentioned [1], [1-1], [1-2], and [2]-[15], which potentiates neprilysin activity.

[17] The pharmaceutical agent; method; or derivative of the above-mentioned [16], wherein the neprilysin activity is enhanced by promoting exteriorization of neprilysin on a cellular surface.

[18] The pharmaceutical agent; method; or derivative of any of the above-mentioned [1], [1-1], [1-2], and [2]-[17], which potentiates α-secretase activity.

[19] The pharmaceutical agent; method; or derivative of any of the above-mentioned [1], [1-1], [1-2], and [2]-[18], which inhibits β-secretase activity.

[20] The pharmaceutical agent; method; or derivative of any of the above-mentioned [1], [1-1], [1-2], and [2]-[15], wherein the polyphenol derivative exhibits at least one kind of effect selected from the group consisting of a neprilysin activity-potentiating effect, an α-secretase activity-potentiating effect and a β-secretase activity inhibitory effect.

[21] An agent for potentiating neprilysin activity and/or α-secretase activity, comprising a polyphenol derivative as an active ingredient.

[21-1] A method of potentiating neprilysin activity and/or α-secretase activity, comprising administering an effective amount of the polyphenol derivative to a subject in need thereof.

[21-2] A polyphenol derivative for use in the potentiating of neprilysin activity and/or α-secretase activity.

[22] The agent of the above-mentioned [21], which exhibits a β-secretase activity inhibitory effect.

[22-1] A method of potentiating a neprilysin activity and/or an α-secretase activity, and inhibiting a β-secretase activity, comprising administering an effective amount of the polyphenol derivative to a subject in need thereof.

[22-2] A polyphenol derivative for use in the potentiating of neprilysin activity and/or α-secretase activity, and inhibition of β-secretase activity.

[23] A β-secretase activity inhibitor comprising a polyphenol derivative as an active ingredient.

[23-1] A method of inhibiting β-secretase activity, comprising administering an effective amount of the polyphenol derivative to a subject in need thereof.

[23-2] A polyphenol derivative for use in the inhibition of β-secretase activity.

[24] The agent of the above-mentioned [23], which exhibits an α-secretase activity-potentiating effect and/or a β-secretase activity inhibitory effect.

[25] The agent; method; or derivative of any of the above-mentioned [21], [21-1], [21-2], [22], [22-1], [22-2], [23], [23-1], [23-2] and [24], wherein the polyphenol derivative is a liposoluble polyphenol derivative.

[26] The agent; method; or derivative of the above-mentioned [25], wherein the liposoluble polyphenol derivative is a liposoluble catechin derivative.

[27] The agent; method; or derivative of the above-mentioned [26], wherein the liposoluble catechin derivative is a compound wherein a liposoluble group is introduced into the EGCg derivative or (−)-epicatechin-3-O-gallate derivative represented by the formula (I):

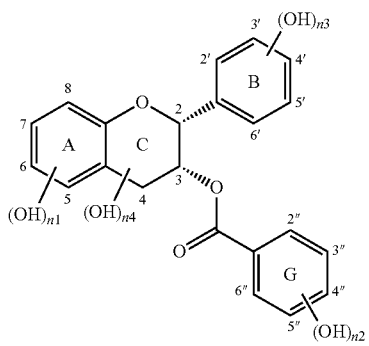

(I)

wherein n1 is the number of hydroxyl groups bonded to ring A, and is an integer of 0-4; n2 is the number of hydroxyl groups bonded to ring G, and is an integer of 0-5; n3 is the number of hydroxyl groups bonded to ring B, and is an integer of 0-5; n4 is the number of hydroxyl groups bonded to ring C, and is 0 or 1; and n1+n2+n3+n4 is two or more.

[28] The agent; method; or derivative of the above-mentioned [26], wherein the liposoluble catechin derivative is a compound wherein a liposoluble group is introduced into the (−)-epigallocatechin derivative or (−)-epicatechin derivative represented by the formula (II):

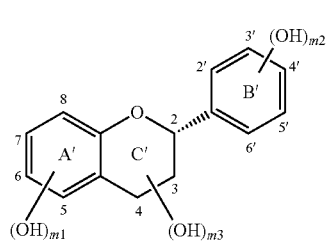

(II)

wherein m1 is the number of hydroxyl groups bonded to ring A', and is an integer of 0-4; m2 is the number of hydroxyl groups bonded to ring B', and is an integer of 0-5; m3 is the number of hydroxyl groups bonded to ring C', and is an integer of 0-2; and m1+m2+m3 is two or more.

[29] The agent; method; or derivative of the above-mentioned [27] or [28], wherein the liposoluble group is selected from the group consisting of a chain hydrocarbon group, a cyclic hydrocarbon group, an aromatic hydrocarbon group, a liposoluble vitamin residue and a sterol residue, each of which optionally has substituent(s).

[30] The agent; method; or derivative of the above-mentioned [27] or [28], wherein the liposoluble group is a chain hydrocarbon group optionally having substituent(s).

[31] The agent; method; or derivative of any of the above-mentioned [27]-[30], wherein the liposoluble group is directly introduced into ring A or ring A' via a C—C bond.

[32] The agent; method; or derivative of any of the above-mentioned [27]-[30], wherein the liposoluble group is introduced without using an S-ester bond or O-ester bond.

[33] The agent; method; or derivative of any of the above-mentioned [27]-[32], wherein the ring C or ring C' has a carbonyl group at the 4-position.

[34] The agent; method; or derivative of the above-mentioned [25], wherein the liposoluble polyphenol derivative has a coefficient of partition (log P) of not less than 1.8-fold that of (−)-epigallocatechin-3-O-gallate used as a control.

[35] The agent; method; or derivative of any of the above-mentioned [21], [21-1], [21-2], [22], [22-1], [22-2], [23], [23-1], [23-2] and [24], wherein the polyphenol derivative is at least one kind selected from the following compound group:

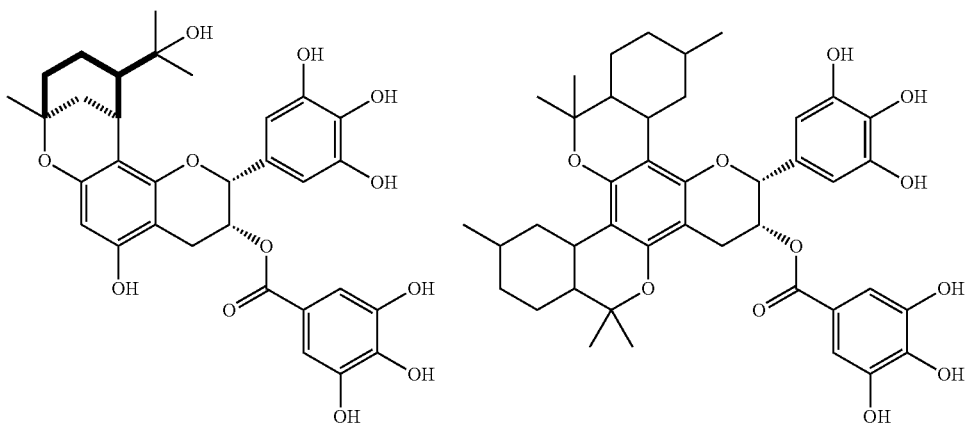

-continued
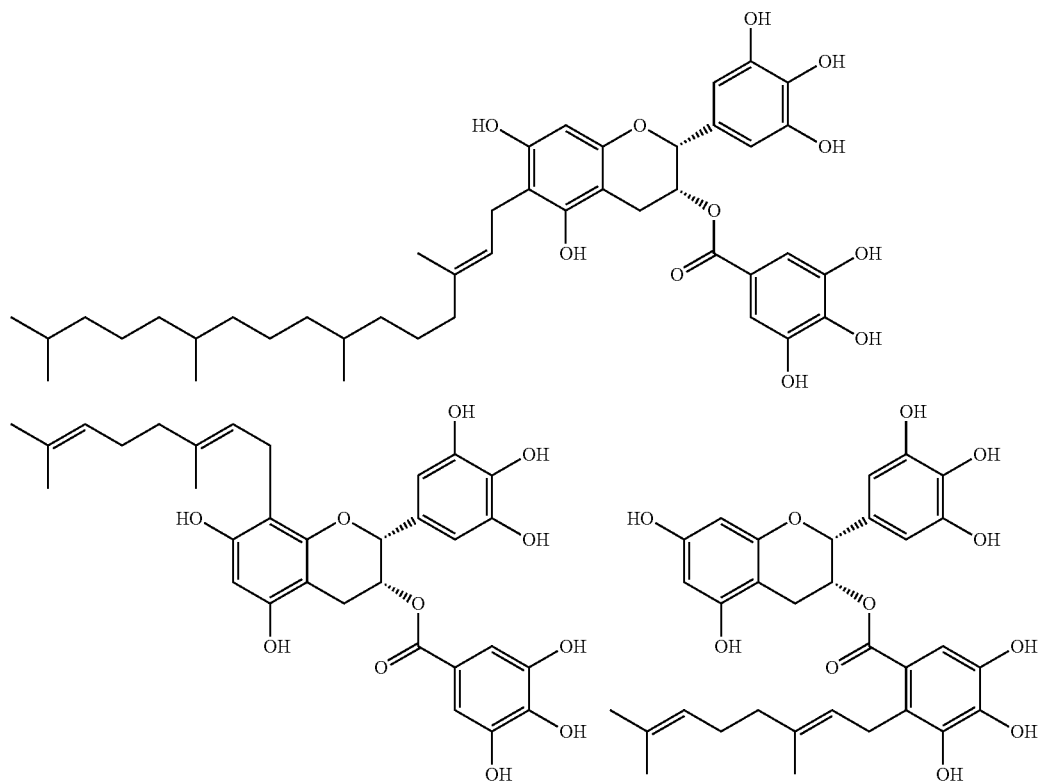
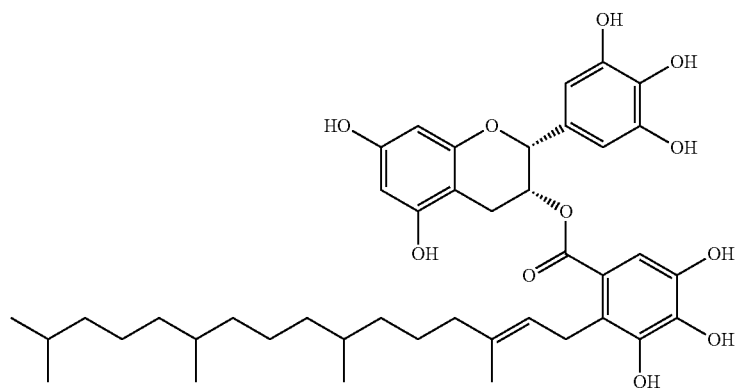
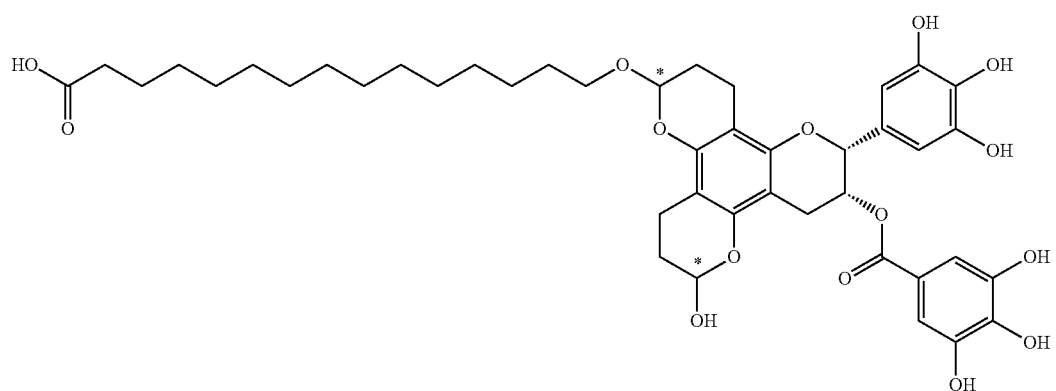

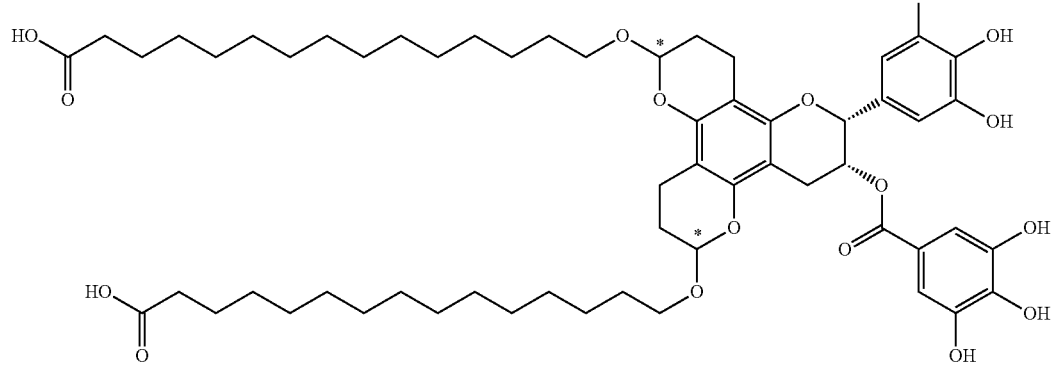
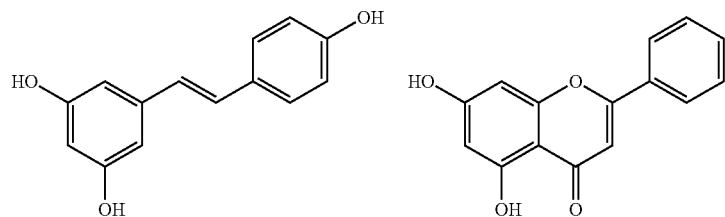
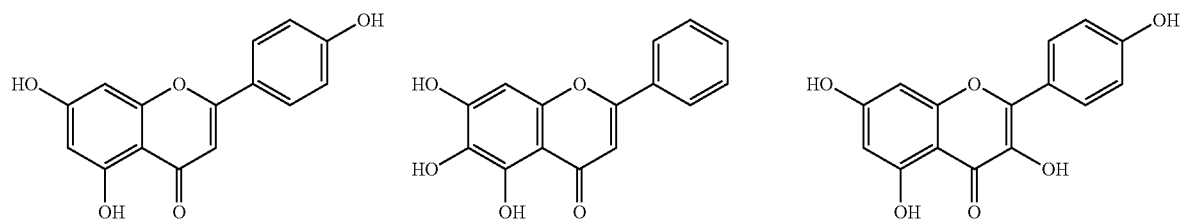
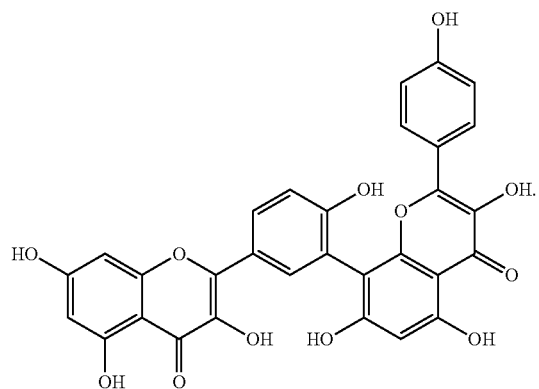
[36] The agent; method; or derivative of any of the above-mentioned [21], [21-1], [21-2], [22], [22-1], [22-2], [23], [23-1], [23-2] and [24], wherein the polyphenol derivative is at least one kind selected from the following compound group:

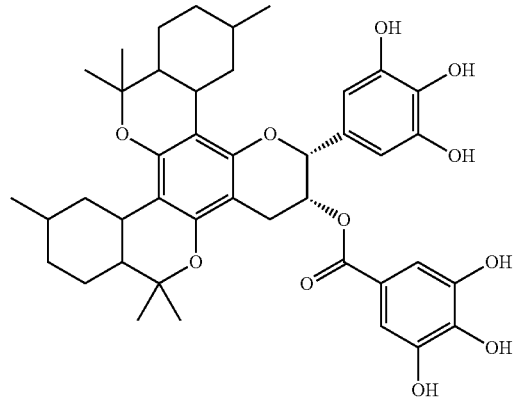
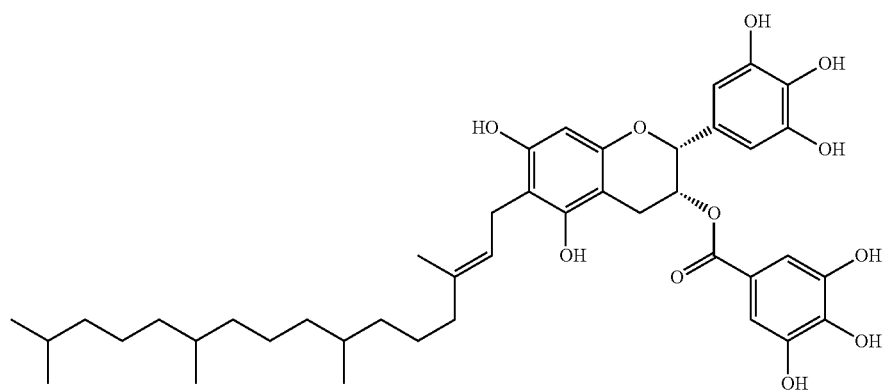
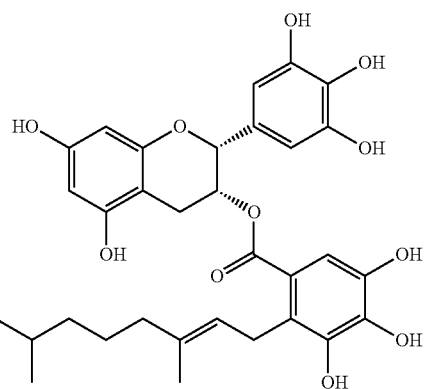
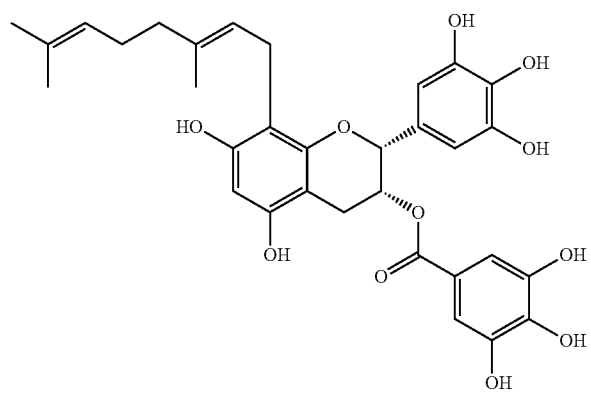

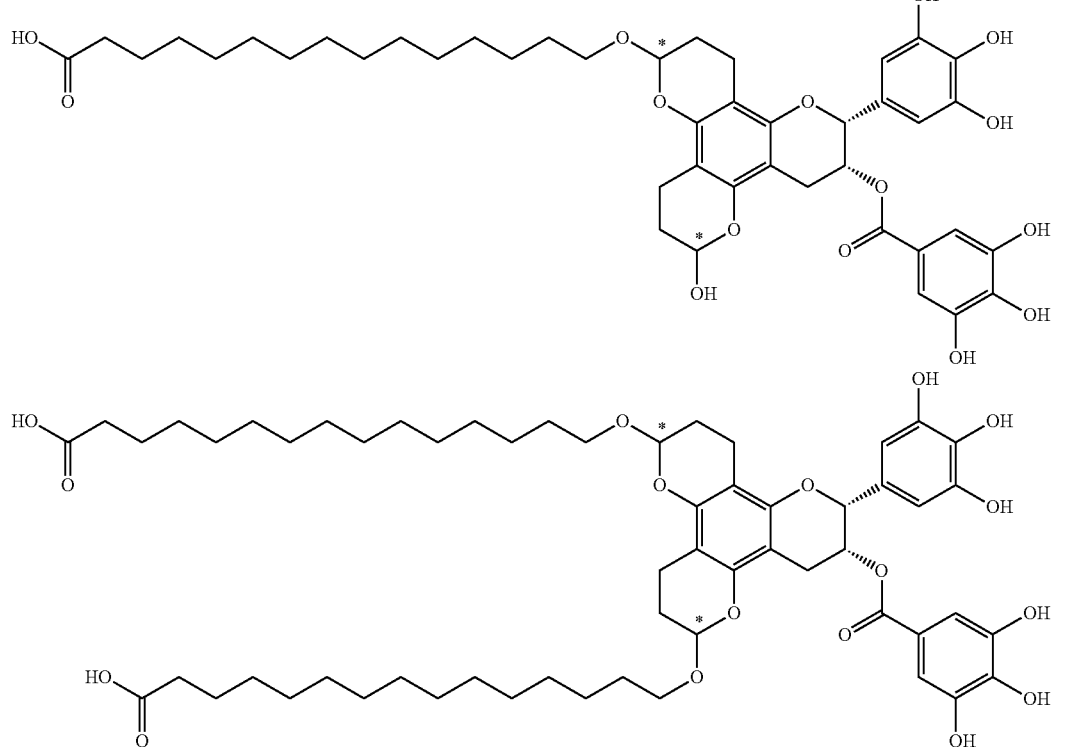

[37] The agent; method; or derivative of any of the above-mentioned [21], [21-1], [21-2], [22], [22-1], [22-2], [23], [23-1], [23-2] and [24], wherein the polyphenol derivative is a catechin derivative or a proanthocyanidin derivative produced by reacting (i) catechin or proanthocyanidin, and (ii) a compound represented by the following formula

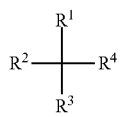

wherein
$R^1$ is a hydrocarbon group;
$R^2$ is hydrogen or hydrocarbon group;
$R^3$ is hydrogen or hydrocarbon group;
$R^4$ is a hydroxyl group, or
$R^3$ and $R^4$ are joined to show a keto group.

[38] The agent; method; or derivative of any of the above-mentioned [21], [21-1], [21-2], [22], [22-1], [22-2], [23], [23-1], [23-2] and [24], wherein the polyphenol derivative is a catechin derivative or a proanthocyanidin derivative produced by reacting (i) catechin or proanthocyanidin, and (ii) 2-hexenal, 2-nonenal, cinnamaldehyde, ferulaldehyde, p-coumaraldehyde, citral, citronellal, geranial, geraniol, farnesal, farnesol, 3,7,11,15-tetramethylhexadecenal, phytol, 3-nonen-2-one or perillaldehyde by adding an acid.

[39] A method of potentiating a neprilysin activity, comprising administering an effective amount of the DYRK1A inhibitor to a subject in need thereof.

[40] The method of the above-mentioned [21], wherein the DYRK1A inhibitor is at least one kind selected from harmine and proINDY.

Effect of the Invention

The present invention obtained by focusing on the degradation system of Aβ can be used as a fundamental therapeutic drug, disease-modifying drug or prophylactic drug for AD. The present invention has a polyphenol skeleton, can utilize research results accumulated up to the present, and enables development of a safer and more effective pharmaceutical agent.

BRIEF DESCRIPTION OF THE DRAWINGS

FIG. 5 schematically shows variation of each element of each polyphenol derivative.

DESCRIPTION OF EMBODIMENTS

Figure 1:
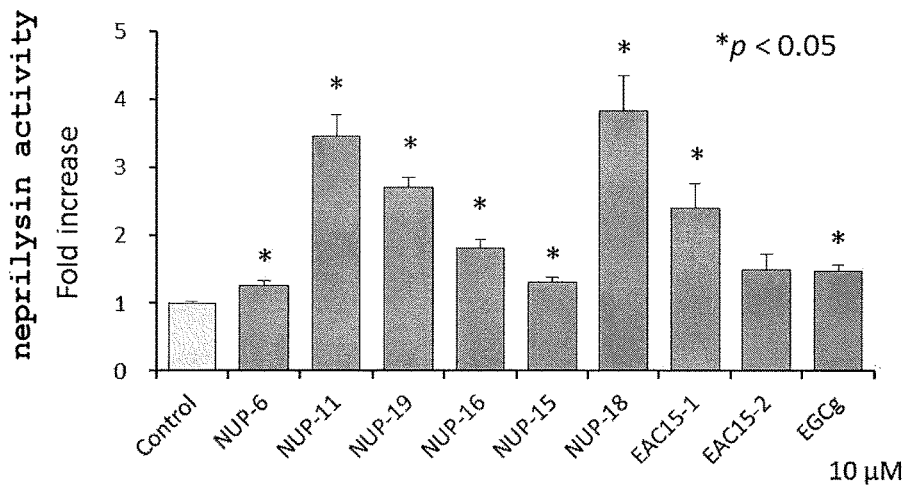
FIG. 1 is a graph showing a neprilysin activity potentiating action of the polyphenol derivative of the present invention. The evaluation is based on the neprilysin activity without addition of a polyphenol derivative as 1. Each derivative was used at a concentration of 1 or 10 μM.
Figure 1:
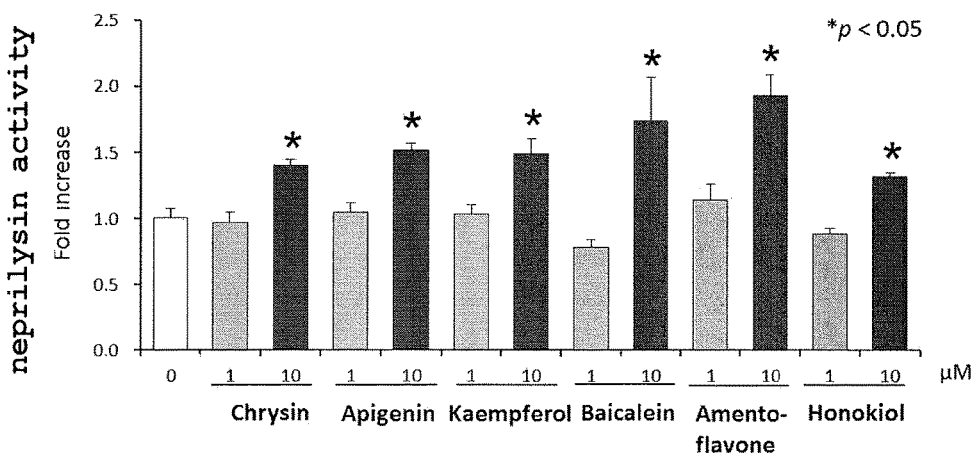

The present invention is more specifically explained in the following.

In the present invention, a polyphenol derivative is used as an active ingredient.

The "polyphenol derivative" in the present invention means a compound having two or more phenolic hydroxyl groups and a derivative thereof, and is not particularly limited as long as it has any one, preferably two, particularly preferably three, of a neprilysin activity potentiating effect, an α-secretase activity potentiating effect and a β-secretase activity inhibiting effect (hereinafter to be also referred to as the polyphenol derivative of the present invention).

In the present specification, the term "potentiating" means an increasing and/or upregulating in the activity and/or efficacy of each enzyme, and the term "inhibiting (inhibitory)" means a decreasing and/or downregulating in the activity and/or efficacy of each enzyme".

For the measurement of the activity of neprilysin, α-secretase and β-secretase, an expression level of a gene encoding neprilysin, α-secretase or β-secretase, or a protein translated from the gene can be used as an index. The expression level of the gene can be measured by RT-PCR, northern blot method and the like, and the amount of a protein translated from the gene can be measured by ELISA, western blot method and the like. Alternatively, the enzyme activity can also be measured directly. The enzyme activity can be presented by the amount of the substrate degraded in a given time.

In the case of neprilysin, the activity thereof can be measured according to, for example, the methods described in JP-A-2002-34596 and JP-A-2004-151079. The substrate of neprilysin is reacted with drug-untreated or drug-treated cells (established cultured cells such as H4 cell, SH-SY5Y cell, HEK cell, Neuro2a cell and the like, nerve cell induced to differentiate from iPS cell, primary culture nerve cells prepared from animals such as mouse, rat and the like, and the like) or tissues (brain tissue prepared from animal such as mouse, rat and the like, and the like), lysate of the above-mentioned cells and tissues, or neprilysin purified from said cell lysate and the like, and evaluated by the amount of the substrate cleaved by neprilysin in the sample (degraded amount of substrate). Examples of the substrate include, but are not limited to, Aβ, enkephalin, substance P, ANP, GRP, endothelin and the like, as well as synthetic substrates such as benzyloxycarbonyl-alanyl-alanyl-leucyl-paranitroanilide, benzyloxycarbonyl-alanyl-alanyl-phenylalanyl-paranitroanilide, benzyloxycarbonyl-glycyl-glycyl-leucyl-paranitroanilide, benzyloxycarbonyl-glycyl-glycyl-phenylalanyl-paranitroanilide, glutaryl-alanyl-alanyl-phenylalanyl-4-methoxy-2-naphthylamide, glutaryl-alanyl-alanyl-phenylalanyl-2-naphthylamide, succinoyl-alanyl-alanyl-phenylalanine-4-methylcoumarin-7-amide, Mca-RPPGFSAFK(Arg-Pro-Pro-Gly-Phe-Ser-Ala-Phe-Lys)-Dnp-OH (R&D Systems, Inc.; SEQ ID NO: 1), 5-FAM/QXLtm520 (AnaSpec, Inc.) and the like. The reaction conditions can be appropriately determined by those of ordinary skill in the art according to the substrate to be used. For example, while the concentration of the substrate varies depending on the substrate to be used, the reaction can be performed at 0.1-1000 μg/ml. The concentration of the substrate is preferably 1-100 μg/ml, more preferably 3-30 μg/ml, in the reaction system. The reaction temperature is preferably 4° C.-45° C., more preferably 20° C.-40° C. While the reaction time varies depending on the substrate to be used and the conditions of the reaction system such as concentration and the like, for example, it can be appropriately selected from 5 min-24 hr. In terms of rapidity, a reaction system capable of measuring in a short time of 5 min-60 min is preferably set. The reaction is preferably performed at neutral pH, i.e., pH6-9, more preferably pH 7-8.

The measurement of the degradation amount of the substrate may be performed by measuring the concentration of the compound obtained by degradation. While the method is not particularly limited, when the absorbance of the compound obtained by degradation increases, or the compound obtained by degradation emits fluorescence, or the compound obtained by degradation reacts with a reagent and emits fluorescence or chemical luminescence, the amount degraded can be measured by measuring the fluorescence intensity or chemical luminescence intensity thereof. In another embodiment, it can be analyzed by thin layer chromatography, HPLC, mass spectrometry and the like, or can also be analyzed by an immunoassay using an antibody that specifically recognizes a peptide fragment or chemical structure of the degradation product. In this case, it is preferable to correct the degradation amount by a measurement value obtained by adding an inhibitor (e.g., thiorphan). The activity of neprilysin may be a degradation amount of a substrate per unit cell amount or total protein (Iwata, N., et al., J. Neurosci. 24(4):991-998, 2004; Ogawa, T., et al., J. Neurochem. 95(4):1156-1166, 2005).

As a method for measuring the expression level of neprilysin at a protein level, lysate of the above-mentioned cells and tissues, or neprilysin purified from said cell lysate and the like as a sample can be analyzed by the western blot method using an antibody specific to neprilysin. In addition, after fixing the above-mentioned cells and tissues, it can also be analyzed by immunostaining of cells and tissues by using an antibody specific to neprilysin (Fukami, S., et al., Neurosci. Res. 43(1):39-56, 2002). As a method for measuring the expression level of neprilysin at an mRNA level, lysate of the above-mentioned cells and tissues as a sample can be analyzed by the northern blot method, quantitative RT-PCR method or real-time PCR method by using an oligonucleotide probe specific to neprilysin (Ogawa, T., et al., J. Neurochem. 95(4):1156-1166, 2005). It is also possible to perform in situ hybridization of the above-mentioned cells and tissues and a labeled oligonucleotide probe specific to neprilysin, and analyze same by autoradiography and immunohistochemical method. Lysate of the above-mentioned cells and tissues or the like, which were knockdowned or knockout neprilysin, or tissue samples were derived from neprilysin-knockout mice, can be used for a negative control.

In the case of α-secretase, its activity can also be measured, for example, according to a previous report (Lopez-Perez E., et al., J Neurochem, 2001). It is evaluated by quantifying the amount of metabolite APPsα, which is cleaved by α-secretase from drug-untreated or drug-treated cells (established cultured cells such as H4 cell, SH-SY5Y cell, HEK cell, Neuro2a cell and the like, nerve cell induced to differentiate from iPS cell, primary culture nerve cells prepared from animals such as mouse, rat and the like, and the like) or tissues (brain tissue prepared from animal such as mouse, rat and the like, and the like) and secreted in the culture supernatant or 105,000×g supernatant, by the western blot method (Yahata, N., et al., PLoS One. 6(9):e25788. 2011) or the ELISA method (Human sAPPα (highly sensitive) Assay Kit-IBL etc., Takara Bio Inc.) using an antibody specific to the carboxyl terminal sequence of APPsα. It can also be measured according to a previous report (Obregon D. F., et al., J Biol Chem, 2006). It is also evaluated by reacting a cell suspension containing an inhibitor of each protease other than metalloprotease with a fluorescent artificial substrate MCA-His-Gln-Lys-Leu-Val-Phe-Phe-Ala-Lys-Dnp-OH (SEQ ID NO: 2) which mimics α-secretase cleavage site or recombinant standard product of endogenous substrate of α-secretase such as APP, APLP1, APLP2 and the like and based on the amount of the cleaved substrate (degraded amount of substrate). The measurement of the degradation amount of the substrate may be performed by measuring the concentration of the compound obtained by degradation. While the method is not particularly limited, when the absorbance of the compound obtained by degradation increases, or the compound obtained by degradation emits fluorescence, or the compound obtained by degradation reacts with a reagent and emits fluorescence or chemical luminescence, the amount degraded can be measured by measuring the fluorescence intensity or chemical luminescence intensity thereof. In another embodiment, it can be analyzed by thin layer chromatography, HPLC, mass spectrometry and the like, or can also be analyzed by an immunoassay using an antibody that specifically recognizes a peptide fragment or chemical structure of the degradation product. In this case, it is preferable to correct the degradation amount by a measurement value obtained by adding an inhibitor (e.g., TAPI-1 [TNF-α Protease Inhibitor-1] or TAPI-2 [TNF-α Protease Inhibitor-2]). The activity of α-secretase may be a degradation amount of a substrate per unit cell amount or total protein (Iwata, N., et al., J. Neurosci. 24(4):991-998, 2004; Ogawa, T., et al., J. Neurochem. 95(4):1156-1166, 2005).

As a method for measuring the expression level of α-secretase at a protein level, lysate of the above-mentioned cells and tissues, or α-secretase purified from said cell lysate and the like as a sample can be analyzed by the western blot method using an antibody specific to ADAM9, ADAM10 or ADAM17 (Yahata, N., et al., PLoS One. 6(9):e25788. 2011). In addition, after fixing the above-mentioned cells and tissues, it can also be analyzed by immunostaining of cells and tissues by using an antibody specific to ADAM9, ADAM10 or ADAM17. As a method for measuring the expression level of α-secretase at an mRNA level, lysate of the above-mentioned cells and tissues as a sample can be analyzed by the northern blot method, quantitative RT-PCR method or real-time PCR method by using an oligonucleotide probe specific to ADAM9, ADAM10 or ADAM17 (Ogawa, T., et al., J. Neurochem. 95(4):1156-1166, 2005). It is also possible to perform in situ hybridization of the above-mentioned cells and tissues and a labeled oligonucleotide probe specific to ADAM9, ADAM10 or ADAM17, and analyze same by autoradiography and immunohistochemical method.

Also in the case of β-secretase, β-secretase activity can be measured using a fluorescent artificial substrate that mimics the β-secretase cleavage site, as in the case of α-secretase, and the expression level of β-secretase at a protein level can be measured using an antibody specific to β-secretase such as an antibody specific to BACE1.

The polyphenol derivative of the present invention is preferably one with enhanced liposolubility, that is, a liposoluble polyphenol derivative, more preferably a liposoluble catechin derivative.

The degree of liposolubility can be shown by numerical values by using a coefficient of partition such as log P (partition coefficient) and the like. While the partition coefficient varies depending on the measurement conditions, when EGCg is used as a control, for example, the log P of the liposoluble polyphenol derivative of the present invention is preferably not less than 1.8-fold that of EGCg.

Generally, liposolubility of an organic compound is improved by introducing a liposoluble group into the compound. A "liposoluble group" means a less polar substituent showing a strong affinity for lipid and small interaction with water. Examples thereof include chain hydrocarbon group (e.g., chain saturated hydrocarbon group such as alkyl group and the like, chain unsaturated hydrocarbon group such as alkenyl group and the like), cyclic hydrocarbon group (e.g., cyclic saturated hydrocarbon group such as cycloalkyl group and the like, cyclic unsaturated hydrocarbon group such as cycloalkenyl group and the like), aromatic hydrocarbon group (e.g., aryl group etc.), liposoluble vitamin residue, sterol residue, a group wherein two or more kinds thereof are bonded and the like. These groups may each have a substituent or such substituents may be bonded to constitute a ring.

The "alkyl group" is a linear or branched chain alkyl group and examples thereof include $C_{3-30}$ alkyl groups (e.g., propyl, isopropyl, butyl, isobutyl, sec-butyl, tert-butyl, 1-methylpropyl, pentyl, isopentyl, 1,2-dimethylpropyl, hexyl, 2-methylpentyl, 3-methylpentyl, 1,2-dimethylbutyl, 1,2,2-trimethylpropyl, heptyl, 3-methylhexyl, octyl, 1-isopropyl-3-methylbutyl, 3-methyl-1-(1-methylethyl)butyl, 2-ethylhexyl, decyl and 4-propylpentyl, 3,7,11,15-tetramethylhexadecyl, 2,6,10,15,19,23-hexamethyltetracosanyl etc.).

The "alkenyl group" is a linear or branched chain and the aforementioned alkyl group having two or more carbon atoms and having one or more unsaturated groups such as double bond and the like. Specific examples thereof include $C_{3-30}$ alkenyl groups (e.g., 1-propenyl, 2-propenyl, 1-butenyl, 2-butenyl, 3-butenyl, 1-pentenyl, 1-hexenyl, 2,6-dimethyl-hepta-1,5-dien-1-yl, 3-phenylpropenyl, 3-(p-hydroxyphenyl)propenyl, geranyl-geranyl, 3,7,11,15-tetramethylhexadecenyl, squalenyl etc.).

This group may be a group induced by removing any hydrogen atom from a naturally-occurring chain unsaturated hydrocarbon having a double bond (e.g., hemiterpene, monoterpene, diterpene, testaterpene, triterpene etc.).

Examples of the "cycloalkyl group" include $C_{3-30}$ cycloalkyl groups such as cyclopropyl, cyclobutyl, cyclopentyl, cyclohexyl (i.e., $C_{3-6}$ cycloalkyl), cycloheptyl, cyclooctyl, bicyclo[2.2.2]octyl and the like. In addition to these, it may be a group induced by removing any hydrogen atom from a natural cycloalkane compound such as steroid and the like.

The "cycloalkenyl group" is the aforementioned cycloalkyl group having one or more unsaturated groups such as double bond and the like. Specific examples thereof include cyclopropenyl, cyclobutyryl, cyclopentynyl, cyclohexynyl, cycloheptynyl, cyclooctynyl, bicyclo[2.2.2]octynyl and the like.

In addition to these, it may be a group induced by removing any hydrogen atom from a natural cycloalkenyl compound such as cholesteryl and oleanoyl group.

The "aryl group" is a monocyclic, bicyclic, tricyclic or tetracyclic carbon cyclic group, wherein at least one ring is aromatic and each ring has 5-8 ring atoms. Specifically, phenyl, indenyl, naphthyl, fluorenyl and the like can be mentioned.

As the "liposoluble vitamin residue", a residue derived from a liposoluble vitamin or a residue derived from a derivative obtained by appropriately converting a hydroxyl group, aldehyde or carboxylic acid, which is a functional group in a liposoluble vitamin, to other reactive functional group can be used. Examples of the liposoluble vitamin include retinoic acid, retinol, retinal, ergosterol, 7-dehydrocholesterol, calciferol, colcalciferol, dihydroergocalciferol, dihydrotachysterol, tocopherol, tocotrienol and the like.

Examples of the "sterol residue" include cholesteryl group (cholesterol residue), cholestaryl group (cholestanol residue), stigmasteryl group (stigmasterol residue), β-sitosteryl group (β-sitosterol residue), lanosteryl group (lanosterol residue), ergosteryl group (ergosterol residue) and the like.

A liposoluble group can be introduced by a method generally used in the pertinent field or a method analogous thereto. For example, when catechin or proanthocyanidin is used as polyphenol, a liposoluble group can be introduced by the method described in patent document 1.

Catechin is a main component of green tea, is well-known to have an antioxidant action, a cholesterol lowering action, an antibacterial action and the like, and thus is generally known to exhibit a favorable influence on health maintenance. The "catechin" in the present invention encompasses any known catechins (e.g., tea catechin etc.). The catechin may be derivatized by a method known per se. The "derivatization" here means to improve function of known catechins by chemical modification such as methylation, esterification, acetone addition, oxidative dimerization, and the like.

Particularly, as tea catechin which is an astringent taste component of tea, epicatechin, epigallocatechin, epicatechingallate, epigallocatechin gallate and the like can be mentioned. As oxidatively dimerized catechin, theasinensins and theaflavins of tea can be mentioned.

The "proanthocyanidin" encompasses any dimers to polymers having a structure in which catechins are carbon-carbon bonded between the C-4 position and the C-8 position. Furthermore, proanthocyanidin in the present invention may be the above-mentioned proanthocyanidin derivatized by a method known per se. The "derivatization" here means to improve function of known proanthocyanidin by chemical modification such as methylation, esterification, and the like.

Particularly, as proanthocyanidin contained in food, procyanidin B-1, procyanidin B-2, procyanidin B-3, procyanidin B-4, procyanidin C-1, prodelphinidin B-1, prodelphinidin B-2 and the like can be mentioned.

One preferable embodiment of the liposoluble catechin derivative of the present invention is a compound in which a liposoluble group is introduced into a EGCg derivative or (−)-epicatechin-3-O-gallate derivative represented by the formula (I) (hereinafter to be also referred to as the formula (I) compound):

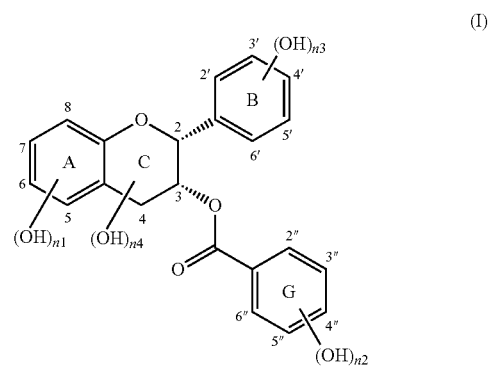

(I)

wherein n1 is the number of hydroxyl groups bonded to ring A, and is an integer of 0-4; n2 is the number of hydroxyl groups bonded to ring G, and is an integer of 0-5; n3 is the number of hydroxyl groups bonded to ring B, and is an integer of 0-5; n4 is the number of hydroxyl groups bonded to ring C, and is 0 or 1; and n1+n2+n3+n4 is two or more.

Here, n1 is preferably 0-2, more preferably 2, further preferably hydroxyl groups are bonded to the 5-position and 7-position of ring A. n2 is preferably 0-3, more preferably 3, further preferably hydroxyl groups are bonded to the 3"-position, 4"-position and 5"-position of G ring. n3 is preferably 0-3, more preferably 3, further preferably hydroxyl groups are bonded to the 3'-position, 4'-position and 5'-position of ring B. n4 is preferably 0.

Another preferable embodiment of the liposoluble catechin derivative of the present invention is a compound in which a liposoluble group is introduced into a (−)-epigallocatechin derivative or (−)-epicatechin derivative represented by the formula (II) (hereinafter to be also referred to as the formula (II) compound):

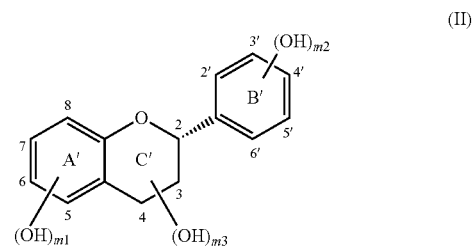

(II)

wherein m1 is the number of hydroxyl groups bonded to ring A', and is an integer of 0-4; m2 is the number of hydroxyl groups bonded to ring B', and is an integer of 0-5; m3 is the number of hydroxyl groups bonded to ring C', and is an integer of 0-2; and m1+m2+m3 is two or more.

Here, m1 is preferably 0-2, more preferably 2, further preferably a hydroxyl groups are bonded to the 5-position and 7-position of ring A'. m2 is preferably 0-3, more preferably 3, further preferably hydroxyl groups are bonded to the 3'-position, 4'-position and 5'-position of ring B'. m3 is preferably 0.

The liposoluble groups to be introduced into the formula (I) compound and the formula (II) compound are those mentioned above. Preferred is a chain hydrocarbon group optionally having substituent(s), and more preferred is an alkyl group or an alkenyl group, each of which optionally has substituent(s). When plural liposoluble groups are to be introduced, they may be the same or different.

Examples of the substituent that the liposoluble group optionally has include, but are not limited to, lower alkyl groups (e.g., $C_{1-6}$ alkyl group such as methyl, ethyl, propyl, isopropyl, butyl, isobutyl, sec-butyl, tert-butyl, pentyl, hexyl and the like; more preferably methyl) optionally substituted by a hydroxyl group, carboxyl group and the like. A liposoluble group and/or a substituent on the liposoluble group, and a hydroxyl group on each ring may be joined to form a ring.

In the formula (I) compound, the liposoluble group can be introduced into one or more of selected from the group consisting of ring A, ring C, ring B and ring G, and may be directly introduced via a C—C bond or introduced via other bond. Preferably, it is directly introduced into ring A via a C—C bond. The liposoluble group is preferably introduced without using an S-ester bond or O-ester bond.

In the formula (II) compound, the liposoluble group can be introduced into one or more of selected from the group consisting of ring A', ring C' and ring B' and may be directly introduced via a C—C bond or introduced via other bond. Preferably, it is directly introduced into ring A' via a C—C bond. The liposoluble group is preferably introduced without using an S-ester bond or O-ester bond.

In the formula (I) compound and the formula (II) compound, a compound having a carbonyl group at the 4-position of ring C or ring C' is also preferable as the liposoluble polyphenol derivative of the present invention.

In the formula (I) compound, ring A, ring C, ring B and ring G optionally have substituent(s) other than a hydroxyl group and a liposoluble group. In the formula (II) compound, ring A', ring C' and ring B' optionally have substituent(s) other than a hydroxyl group and a liposoluble group. Examples of the substituent that each ring optionally has include, but are not limited to, an oxo group and the like.

Specific examples of a compound preferable as the polyphenol derivative of the present invention are the following.

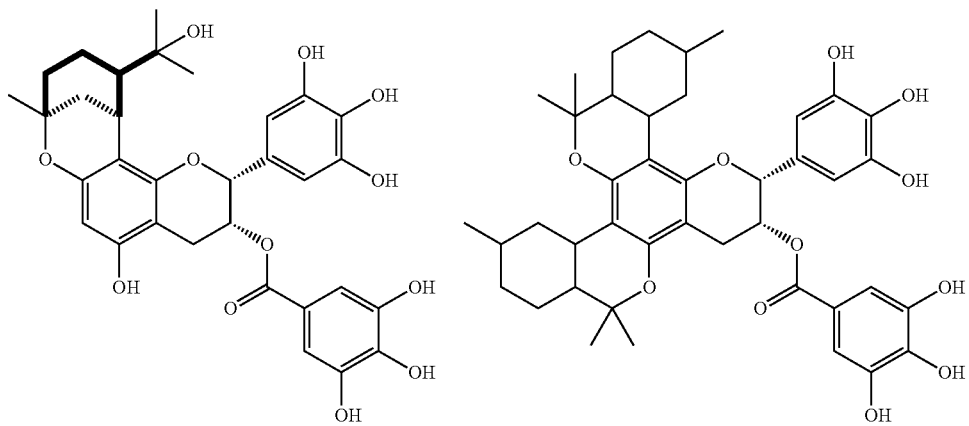

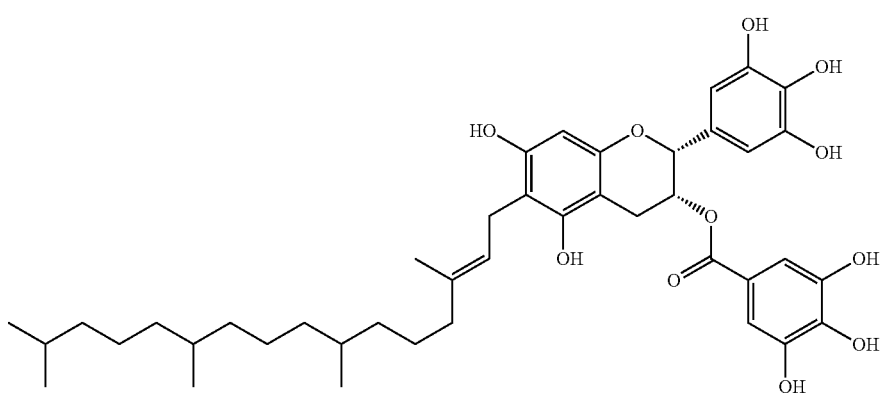

33 34
-continued
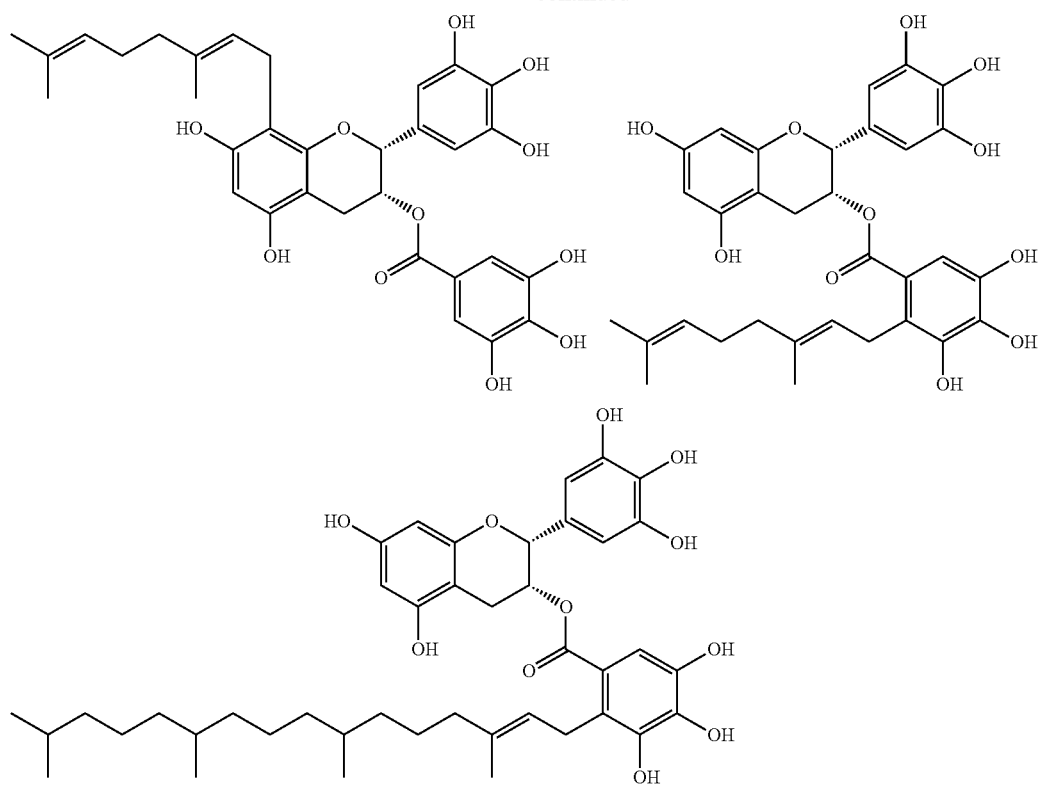
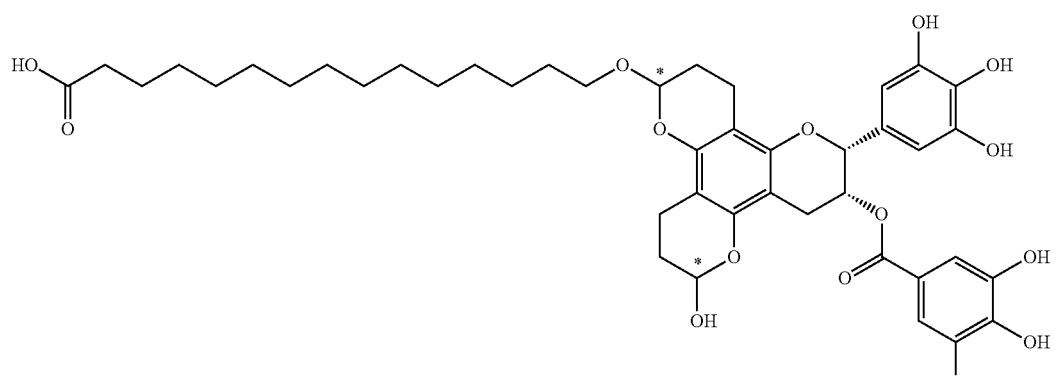
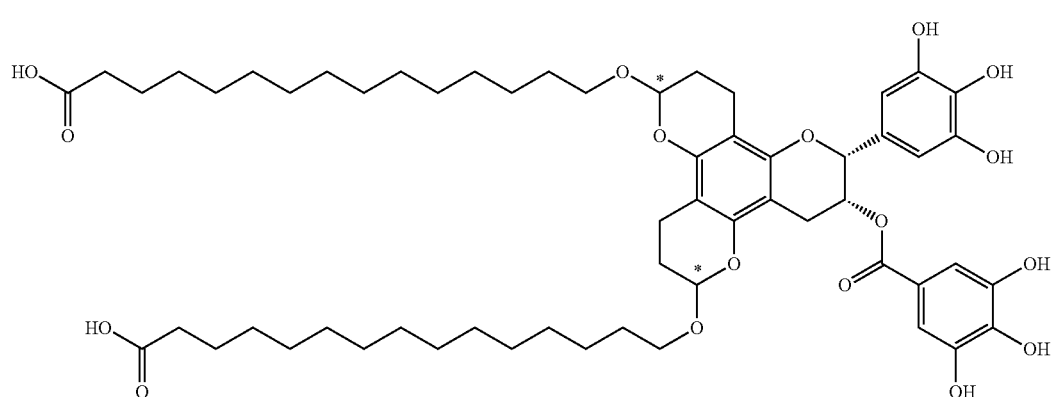

-continued
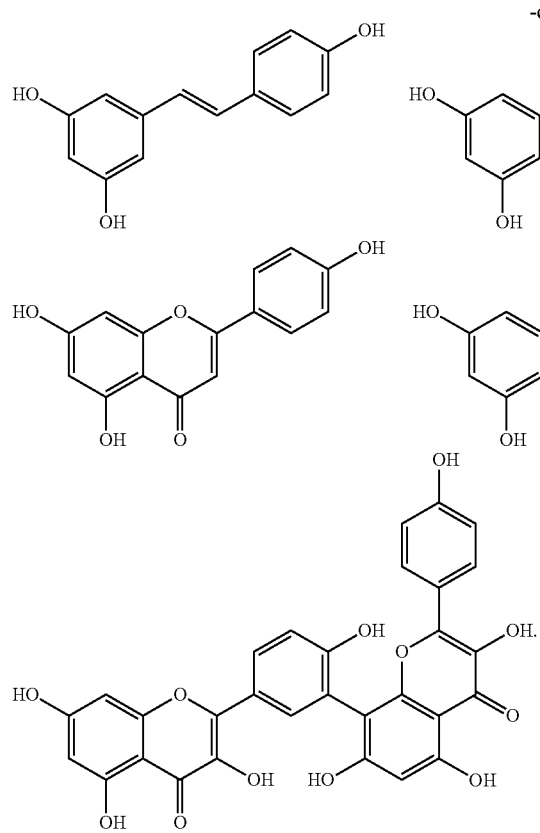
Of these,
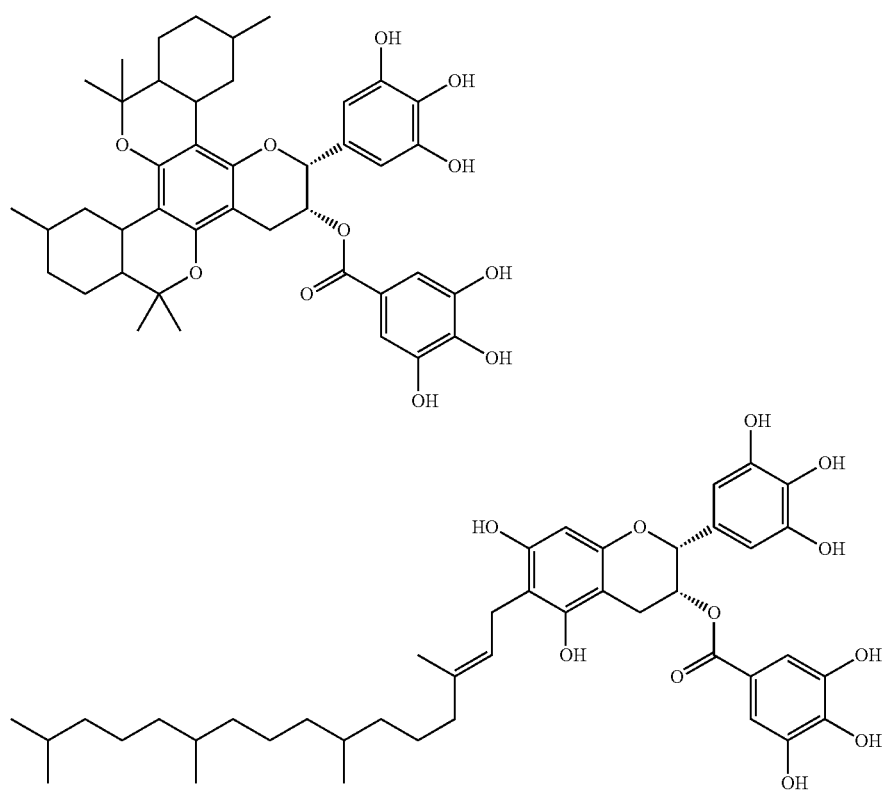

-continued
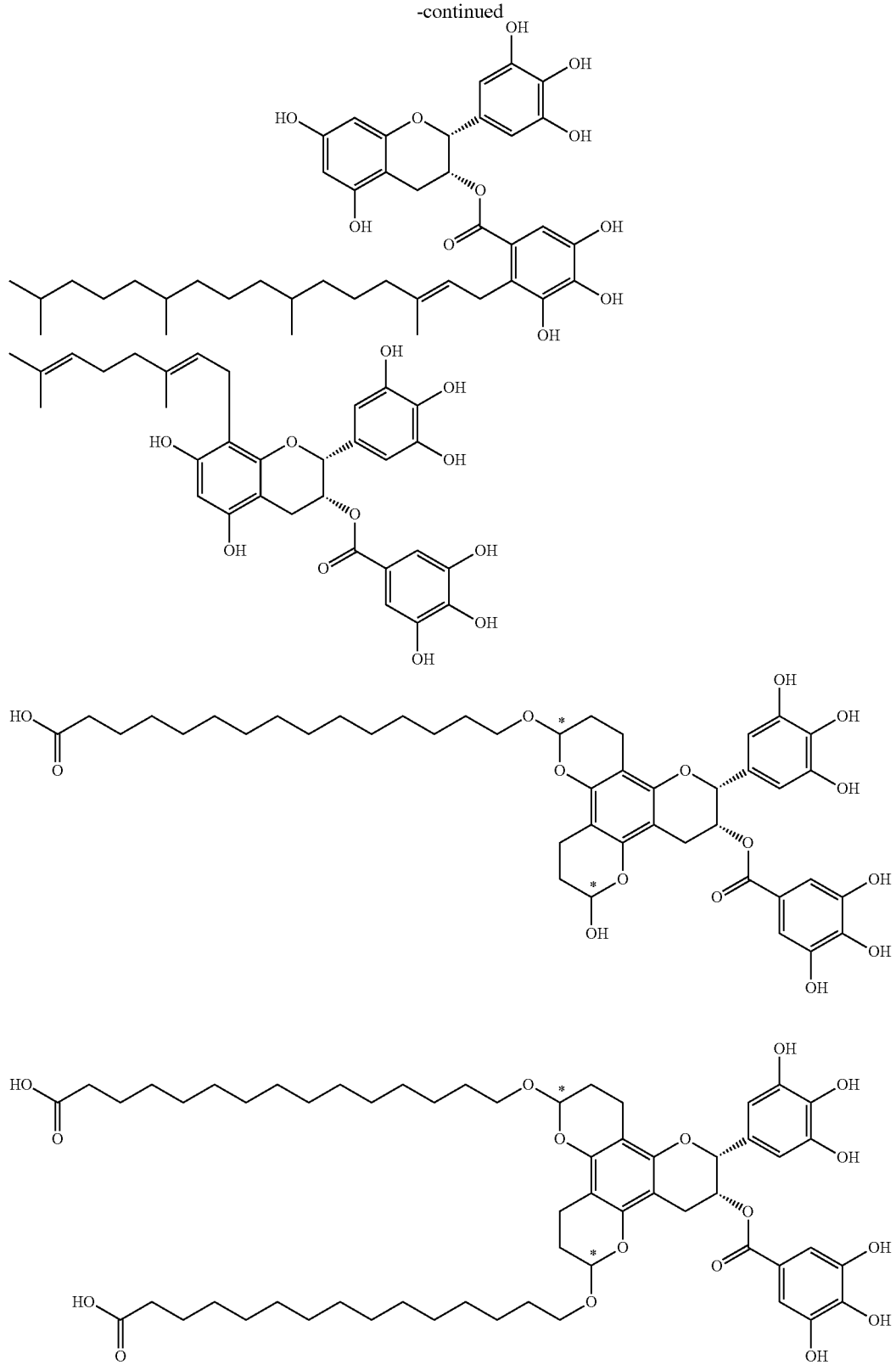
are preferable.
One embodiment of the polyphenol derivative of the present invention is a catechin derivative or a proanthocyanidin derivative produced by reacting (i) catechin or proanthocyanidin, and (ii) a compound represented by the following formula

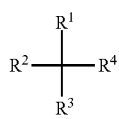

wherein
R¹ is a hydrocarbon group;
R² is hydrogen or hydrocarbon group;
R³ is hydrogen or hydrocarbon group;
R⁴ is a hydroxyl group, or
R³ and R⁴ are joined to show a keto group.

Examples of the "hydrocarbon group" include a chain saturated hydrocarbon group (e.g., alkyl group etc.), a chain unsaturated hydrocarbon group (e.g., alkenyl group etc.), a cyclic saturated hydrocarbon group (e.g., cycloalkyl group etc.), a cyclic unsaturated hydrocarbon group (e.g., cycloalkenyl group etc.), an aromatic hydrocarbon group (e.g., aryl group etc.) and the like, which are as defined for the groups recited as examples of the above-mentioned "liposoluble group".

Specifically, the compound can be produced by the method described in patent document 1.

One embodiment of the polyphenol derivative of the present invention is, for example, a catechin derivative or a proanthocyanidin derivative produced by reacting (i) catechin or proanthocyanidin, and (ii) 2-hexenal, 2-nonenal, cinnamaldehyde, ferulaldehyde, p-coumaraldehyde, citral, citronellal, geranial, geraniol, farnesal, farnesol, 3,7,11,15-tetramethylhexadecenal, phytol, 3-nonen-2-one, perillaldehyde or acrolein by adding an acid.

Specifically, the compound can be produced by the method described in patent document 1.

The compound can also be produced by binding (i) and (ii) and further binding (ii) to the resultant product. For example, the compound can also be produced by binding catechin to acrolein and further binding alcohols, amines, carboxylic acids, thiols and the like are bonded to the obtained substance (see Examples).

The polyphenol derivative of the present invention may be in the form of a salt. For example, salts with physiologically acceptable acid (e.g., inorganic acid, organic acid), base (e.g., alkali metal salt) and the like are used, and a physiologically acceptable acid addition salt is particularly preferable. Examples of such salt to be used include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, trifluoroacetic acid) and the like.

When the polyphenol derivative of the present invention has an isomer such as optical isomer, stereoisomer, regio isomer, rotamer and the like, either one of the isomers and a mixture of isomers can also be used. When the polyphenol derivative of the present invention has a structural isomer and a geometric isomer such as tautomer and the like, any isomer can be used.

The polyphenol derivative of the present invention may be labeled with an isotope (e.g., $^3$H, $^{14}$C, $^{35}$S, $^{125}$I etc.) and the like.

Since the polyphenol derivative of the present invention shows a neprilysin activity-potentiating effect and/or an α-secretase activity-potentiating effect, and/or a β-secretase activity inhibitory effect, it is useful as a neprilysin activity and/or α-secretase activity enhancer, or a β-secretase activity inhibitor (hereinafter to be also each referred to as the enhancer of the present invention or the inhibitor of the present invention, and collectively called to as the agent of the present invention). Due to such actions, the polyphenol derivative of the present invention is useful as a pharmaceutical agent for the prophylaxis and/or treatment of AD (hereinafter to be also referred to as the pharmaceutical agent of the present invention). The polyphenol derivative of the present invention, and an agent and a pharmaceutical agent containing same as an active ingredient are also generically referred to as the pharmaceutical agent of the present invention. The agent of the present invention can be, in addition to the use as a pharmaceutical agent for the prophylaxis and/or treatment of AD, a tool leading to the elucidation of the onset mechanism of AD and the development of a novel anti-AD drug.

Furthermore, the present invention can provide a method for the prophylaxis and/or treatment of AD, comprising administering an effective amount of the polyphenol derivative of the present invention to a patient in need thereof.

Furthermore, the present invention can provide a method of potentiating neprilysin activity and/or α-secretase activity, comprising administering an effective amount of the polyphenol derivative of the present invention to a subject in need thereof. The method may accompany inhibition of β-secretase activity, and preferably accompanies inhibition of β-secretase activity.

Furthermore, the present invention can provide a method of inhibiting β-secretase activity, comprising administering an effective amount of the polyphenol derivative of the present invention to a subject in need thereof. The method may accompany potentiating of neprilysin activity and/or α-secretase activity, and preferably accompanies same.

Since the polyphenol derivative of the present invention has a neprilysin activity-potentiating action, it can be applied to not only AD but also other diseases showing amyloid pathology, and malignant tumor and cancer of peripheral tissues in which substrate peptide of neprilysin is involved.

Since the active ingredient of the pharmaceutical agent of the present invention is a polyphenol derivative, it is expected to show low toxicity. It can be administered orally or parenterally (e.g., intravascular administration, subcutaneous administration, etc.) as a liquid or as a pharmaceutical composition in a suitable dosage form to human or other warm-blooded animals (e.g., mouse, rat, rabbit, sheep, swine, bovine, horse, goat, cat, dog, monkey, avian, etc.).

The polyphenol derivative of the present invention itself may be administered, or may be administered as a suitable pharmaceutical composition. Furthermore, the polyphenol derivative of the present invention may be in the form of a mixture of two or more kinds of the above-mentioned respective polyphenol derivatives as desired. The pharmaceutical composition to be used for administration may contain the polyphenol derivative of the present invention and a pharmacologically acceptable carrier, a diluent or an excipient. Such pharmaceutical composition is provided in a dosage form suitable for oral or parenteral administration.

As a composition for parenteral administration, for example, injection, suppository and the like are used, and the injection may include the dosage forms of intravenous injection, subcutaneous injection, intradermal injection, intramuscular injection, drip injection, intrathecal injection, and the like. Such injection can be prepared according to a known method. Injection can be prepared, for example, by dissolving, suspending or emulsifying the improving agent of the present invention in a sterile aqueous solution or an oily solution generally used for injection. As the aqueous solution for injection, for example, saline, isotonic solution containing glucose and other auxiliary agents, and the like are used, which may be used in combination with a suitable solubilizing agent, for example, alcohol (e.g. ethanol), polyalcohol (e.g., propylene glycol, polyethylene glycol), nonionic surfactant [e.g., polysorbate80, HCO-50 (polyoxyethylene (50 mol) adduct of hydrogenated castor oil)] and the like. As the oily solution, sesame oil, soybean oil and the like are used and, as a solubilizing agent, benzyl benzoate, benzyl alcohol and the like may be used in combination. A prepared injection is preferably filled in a suitable ampoule. A suppository to be used for rectal administration may be prepared by mixing the above-mentioned polyphenol derivative with a general suppository base.

The polyphenol derivative of the present invention can also be directly administered intracerebrally by surgical operation and the like.

Examples of the composition for oral administration include solid or liquid dosage forms, which are specifically tablet (including sugar-coated tablet, film-coated tablet), pill, granule, powder, capsule (including soft capsule), syrup, emulsion, suspension and the like. Such composition is produced by a known method, and may contain a carrier, a diluent or an excipient generally used in the pharmaceutical field. As the carrier and excipient for tablets, lactose, starch, saccharose, and magnesium stearate are used.

The above-mentioned parenteral or oral pharmaceutical composition is conveniently prepared into a dosage form in a dosage unit compatible with the dose of the polyphenol derivative as the active ingredient. Examples of such dosage form in the dosage unit include tablet, pill, capsule, injection (ampoule), and suppository.

While the dose of the pharmaceutical agent of the present invention varies depending on the subject of administration, symptom, administration route and the like, for example, when it is used for the treatment or prophylaxis of AD in an adult, generally about 1-50 mg/kg body weight, preferably about 10-30 mg/kg body weight, further preferably about 15-25 mg/kg body weight, of the pharmaceutical agent of the present invention as a daily dose is conveniently administered orally in about 1-5 portions per day, preferably 1-3 portions per day. For other administration routes, amounts in accordance therewith can be administered. When the symptom is particularly severe, the amount may be increased according to the symptom.

Each of the above-mentioned compositions may contain other active ingredients unless undesirable interaction is caused by blending with the polyphenol derivative of the present invention.

In addition, each of the above-mentioned compositions may be used in combination with other compounds effective for the prophylaxis and/or treatment of AD and other than the polyphenol derivative, unless undesirable interaction is caused by blending with the polyphenol derivative of the present invention (hereinafter to be also referred to as concomitant compound). Examples of the concomitant compound include drugs already sold and approved in Japan such as acetylcholinesterase inhibitors (donepezil, galanthamine, rivastigmine), NMDA receptor antagonists of glutamic acid (memantine) and the like, as well as amyloid vaccine, α-secretase activity enhancer, BSI, GSI, γ-secretase modulator and the like, which are under study in recent years.

While the α-secretase activity enhancer is not particularly limited, for example, retinoid and the like can be mentioned.

While the BSI is not particularly limited, for example, β-secretase inhibitor IV, VTP-37948, E2609, JNJ-54861911, LY3314814, thalidomide, MK-8931 and the like can be mentioned. While the GSI is not particularly limited, for example, Compound E, ACPC ((S,S)-2-aminocyclopentanecarboxylic acid), semagacestat and the like can be mentioned.

While the γ-secretase modulator is not particularly limited, for example, pinitol, EVP-0962 and the like can be mentioned. The amyloid vaccine can be either a passive immunity vaccine which directly administers the antibody or an active immunity vaccine which administers the Aβ with an adjuvant.

Particularly, BSIs and GSIs have strong side effects. When combined with the polyphenol derivative of the present invention, the use concentration can be reduced and the risk of side effects can be dispersed.

The present invention is explained in detail in the following by referring to Examples which are not to be construed as limitative. Unless particularly indicated, the reagent and the like to be used are commercially available.

EXAMPLES

Example 1

(Materials and Method)
1. Polyphenol Derivative

The following polyphenol derivative was prepared as a test compound, and used at a given concentration. The coefficient of partition of each compound for octanol is in accordance with a previous report (Fudouji, R et al., J. Agric. Food Chem. 57(14):6417-6424, 2009).

TABLE 1

| test compound | structural formula/ compound name | preparation method/ supplier/ reference document | log P octanol |
|---|---|---|---|
| EGCg | 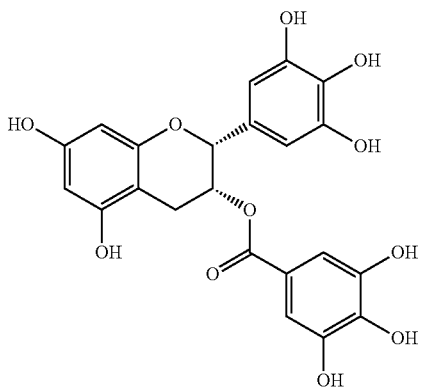 [SMILES: O=C(O[C@@H]1Cc2c(O)cc(O)cc2O[C@@H]1c1cc(O)c(O)c(O)c1)c1cc(O)c(O)c(O)c1]<br>(-)-epigallocatechin-3-O-gallate | purified according to previous report (Nonaka, G et al., Chem. Pharm. Bull. 1983, 31, 3906-3914) by separating from green tea and crystallizing from water | 1.00 |

TABLE 1-continued
| test compound | structural formula/ compound name | preparation method/ supplier/ reference document | log P octanol |
|---|---|---|---|
| NUP-6 | 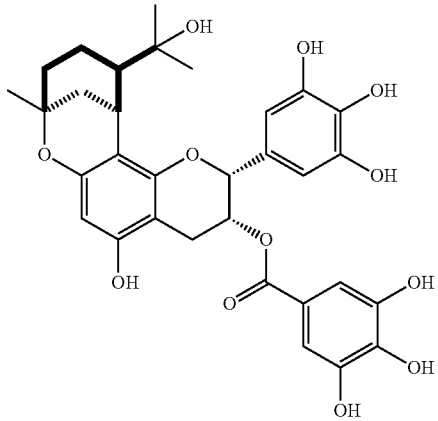 | prepared according to patent document 1, Example 2 (compound 2) | 1.85 |
| NUP-11 | 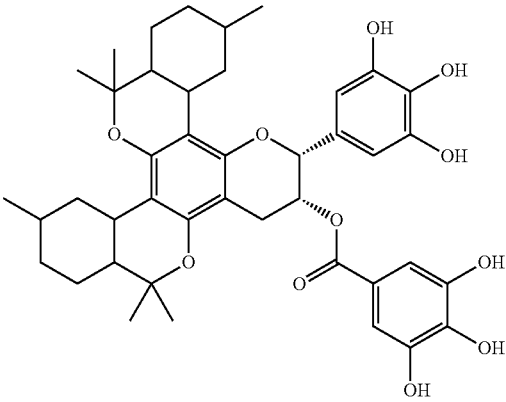 [SMILES: CC1CCC2C(C1)c1c(c3c(c4c1OC(C)(C)C1CCC(C)CC41)O[C@H](c1cc(O)c(O)c(O)c1)[C@H](OC(=O)c1cc(O)c(O)c(O)c1)C3)OC2(C)C] | prepared according to patent document 1, Example 3 (compound 6) | >10 |
| NUP-19 | 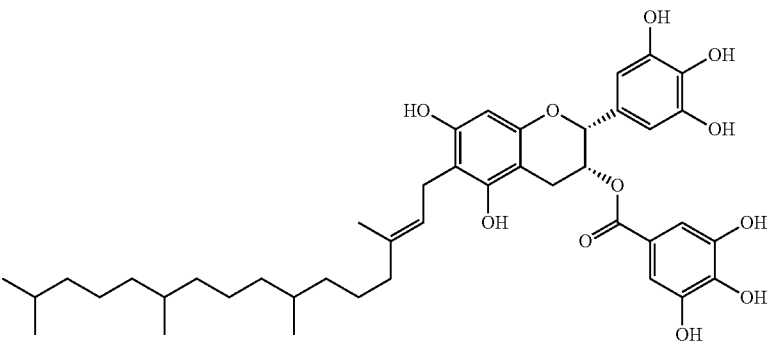 [SMILES: C/C(=C\Cc1c(O)cc2c(c1O)C[C@@H](OC(=O)c1cc(O)c(O)c(O)c1)[C@@H](c1cc(O)c(O)c(O)c1)O2)CCCC(C)CCCC(C)CCCC(C)C] | prepared according to patent document 1, Example 7, non-patent document 10 | >10 |

TABLE 1-continued

| test compound | structural formula/ compound name | preparation method/ supplier/ reference document | log P octanol |
|---|---|---|---|
| NUP-16 | | prepared according to patent document 1, Example 7 (compound 8) | 2.55 |
| NUP-15 | | prepared according to patent document 1, Example 7 (compound 9) | |
| NUP-18 | | prepared according to patent document 1, Example 7, non-patent document 10 | |
| NUP-E15-1 | | see Synthetic Example below | |

TABLE 1-continued

| test compound | structural formula/ compound name | preparation method/ supplier/ reference document | log P octanol |
|---|---|---|---|
| | 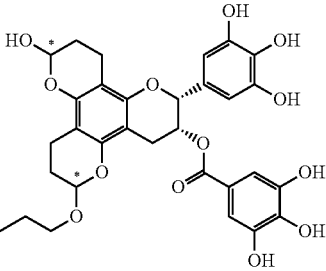 | | |
| NUP-E15-2 | 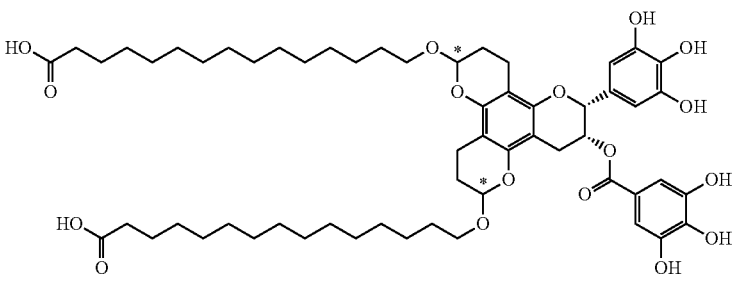 [SMILES: O=C(O)CCCCCCCCCCCCCCOC1CCc2c(c3c(c4c2O[C@H](c2cc(O)c(O)c(O)c2)[C@H](OC(=O)c2cc(O)c(O)c(O)c2)C4)OC(OCCCCCCCCCCCCCCC(=O)O)CC3)O1] | see Synthetic Example below | |
| Resveratrol | 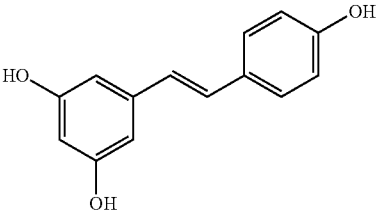 [SMILES: Oc1ccc(/C=C/c2cc(O)cc(O)c2)cc1] | commercially available product was used | |
| Chrysin | 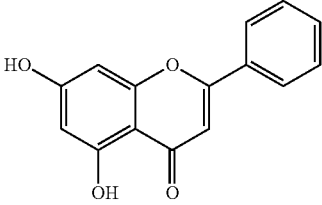 [SMILES: O=c1cc(-c2ccccc2)oc2cc(O)cc(O)c12] | commercially available product was used | |
| Apigenin | 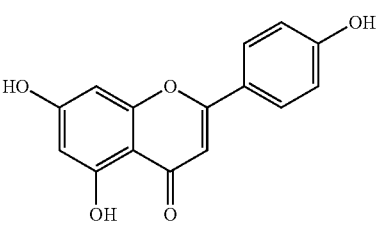 [SMILES: O=c1cc(-c2ccc(O)cc2)oc2cc(O)cc(O)c12] | commercially available product was used | |
| Kaempferol | 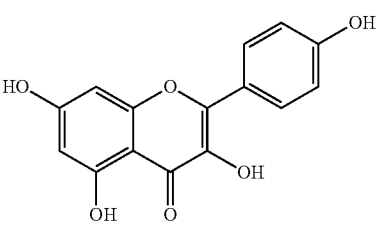 [SMILES: O=c1c(O)c(-c2ccc(O)cc2)oc2cc(O)cc(O)c12] | commercially available product was used | |

TABLE 1-continued

| test compound | structural formula/ compound name | preparation method/ supplier/ reference document | log P octanol |
|---|---|---|---|
| Baicalein | | commercially available product was used | |
| Amento-flavone | | commercially available product was used | |
| Honokiol | | commercially available product was used | |

As the polyphenol derivative obtained by binding catechin to acrolein (Acr) to obtain a substance and further binding alcohols, amines, carboxylic acids, thiols and the like to the obtained substance, for example, NUP-E15-1 (EGCg-Acr-monoC15) and NUP-E15-2 (EGCg-Acr-diC15) can be mentioned. These compounds can be produced as follows.

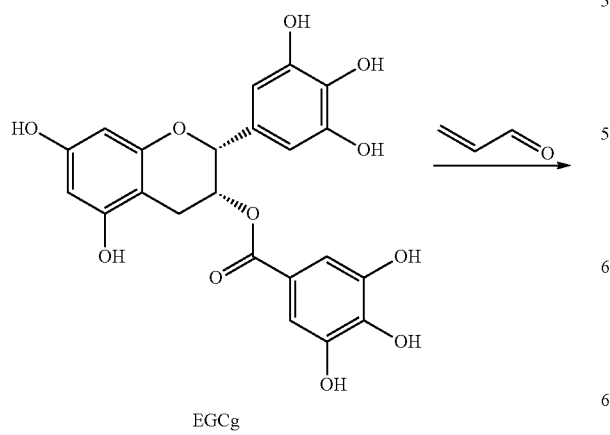

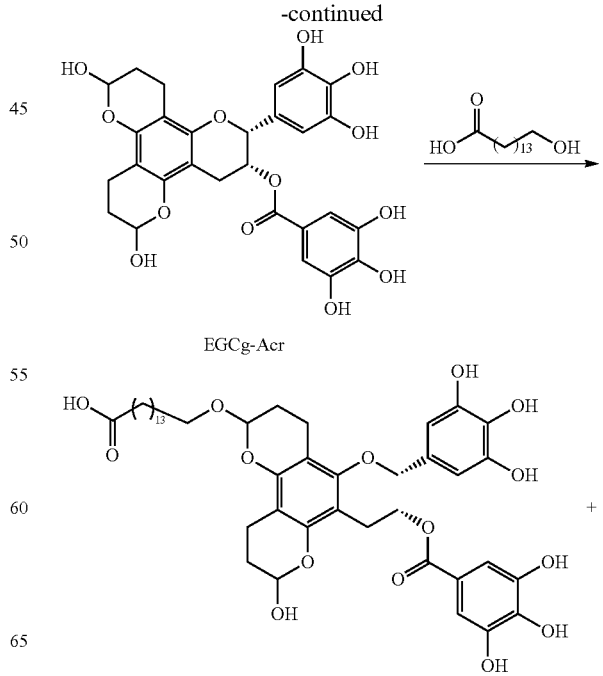

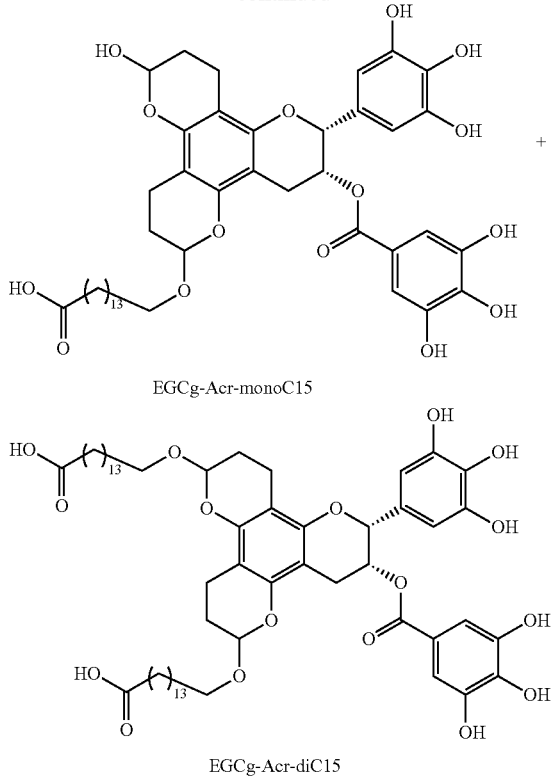

EGCg-Acr-monoC15

EGCg-Acr-diC15

Epigallocatechin gallate (EGCg; 1 mmol) was dissolved in acrolein (2 ml), and the mixture was heated at 70° C. for 1 hr. The reaction mixture was directly applied to Sephadex LH-20 column (2 cm×15 cm) swollen with ethanol, and successively eluted with ethanol, and ethanol-acetone-water mixture (8:1:1, 6:2:2, 0:1:1, v/v/v) to give an acrolein conjugate (EGCg-Acr; 0.78 mmol, 78%). Then, the acrolein conjugate (114 mg, 0.2 mmol) and 15-hydroxypentadecanoic acid (0.2 mmol) were dissolved in acetone (2 ml) containing trifluoroacetic acid (5%), and the mixture was heated at 60° C. for 7 hr. The reaction resultant product was subjected to silica gel column (2 cm×10 cm), separated from chloroform-methanol (100:0, 90:10, 85:15, 80:20, 75:25, 70:30, v/v) to give a monosubstituted form (EGCg-Acr-monoC15; 46.8 mg, 0.082 mmol, 29%) and di-substituted form (EGCg-Acr-diC15; 18.5 mg, 0.018 mmol, 9%).

EGCg-Acr
White Amorphous Powder
$[\alpha]_D^{29}$ -146.8 (c=0.10, MeOH)
FAB-MS m/z: 571[M+H]$^+$
HR-FAB-MS m/z: 571.1450[M+H]$^+$ ($C_{28}H_{27}O_{13}$ requires 571.1452)
UV $\lambda_{max}^{MeOH}$ nm (log ε): 210 (3.87), 275 (2.98)
IR $v_{max}$ cm$^{-1}$: 3374, 2954, 2856, 1688, 1613, 1534, 1453.
$^1$H-NMR (400 MHz, acetone-d$_6$) δ: 5.05 (1H, br s, H-2), 5.54 (1H, br s, H-3), 2.84 (1H, br d, H-4), 3.00 (m, H-4), 6.56 (2H, br s, B-ring, H-2, 6), 7.00 (2H, br s, galloyl-H-2,6). 5.54 (2H, m, Acr-1,1'), 1.87 (4H, m, Acr-2,2'), 2.56, 2.75 (m, Acr-3,3').
$^{13}$C-NMR (100 MHz, acetone-d$_6$) δ: 77.7 (C-2), 69.1 (C-3), 28.0 (C-4), 99.6 (C-4a), 151.2 (C-5), 103.3 (C-6), 151.2 (C-7), 102.6 (C-8), 149.7 (C-8a), 130.8 (B-ring C-1), 106.4 (B-ring C-2,6), 146.2 (B-ring C-3,5), 133.0 (B-ring C-4), 121.8 (galloyl C-1), 109.7 (galloylC-2,6), 145.8 (galloyl C-3,5), 138.7 (galloylC-4), 166.2 (galloylC-7). 92.9 (Acr-C-1,1'), 26.7 (Acr-C-2,2'), 15.9 (Acr-C-3,3').

EGCg-Acr-monoC15
White Amorphous Powder
$[\alpha]_D^{29}$ -102.7 (c=0.10, MeOH)
FAB-MS m/z: 849[M+K]$^+$
HR-FAB-MS m/z: 849.3092[M+K]$^+$ ($C_{43}H_{54}O_{15}K$ requires 849.3100)
UV $\lambda_{max}^{MeOH}$ nm (log ε): 209 (3.89), 275 (3.01)
IR $v_{max}$ cm$^{-1}$: 3250, 2923, 2851, 1682, 1615, 1536, 1455.
$^1$H-NMR (400 MHz, acetone-d$_6$) δ: 5.06 (H-2), 5.20, 5.28 (H-3), 2.96 (H-4), 6.66 (brs, B-ring H-2,6), 6.99 (brs, galloyl-C-2,6), 5.54 (m, Acr-H-1,1'), 1.90 (m, Acr-H-2,2'), 2.60 (m, Acr-H-3,3'), 1.2-1.6 (m, CH$_2$) 3.55, 3.88 (CH$_2$—O—).
$^{13}$C-NMR (100 MHz, acetone-d$_6$) δ: 77.6 (C-2), 68.5-69.3 (C-3), 28.0 (C-4), 100.0 (C-4a), 151.2 (C-5), 103.0-103.7 (C-6,8), 151.2 (C-7), 149.5 (C-8a), 130.9 (B-ring C-1), 106.4 (B-ring C-2,6), 146.2 (B-ring C-3,5), 132.9 (B-ring C-4), 121.7 (galloyl C-1), 110.0 (galloylC-2,6), 145.8 (galloyl C-3,5), 138.8 (galloylC-4), 166.2 (galloylC-7). 92.8, 97.9 (Acr-C-1,1'), 26.8 (Acr-C-2,2'), 15.9 (Acr-C-3,3'), 175.0 (COOH), 25.6, 26.7, 29.2, 29.6, 29.8, 30.0, 30.2, 30.4, 34.2 (CH$_2$), 68.5-69.3 (CH$_2$O).

EGCg-Acr-diC15
White Amorphous Powder
$[\alpha]_D^{28}$ -86.6 (c=0.10, MeOH)
FAB-MS m/z: 1089[M+K]$^+$
HR-FAB-MS m/z: 1089.5195[M+K]$^+$ ($C_{58}H_{82}O_{17}K$ requires 1089.5189)
UV $\lambda_{max}^{MeOH}$ nm (log ε): 209 (3.77), 275 (3.05)
IR $v_{max}$ cm$^{-1}$: 3330, 2924, 2852, 1703, 1615, 1536, 1459.
$^1$H-NMR (400 MHz, acetone-d$_6$) δ: 5.04, 5.08 (H-2), 5.20, 5.26 (H-3), 2.90-3.10 (H-4), 6.66 (brs, B-ring H-2,6), 6.98, 7.01 (galloyl-C-2, 6), 5.55 (m, Acr-H-1,1'), 1.90 (m, Acr-H-2,2'), 2.50-2.85 (m, Acr-H-3, 3'), 1.2-1.6 (m, CH$_2$) 3.50-3.85 (CH$_2$—O—).
$^{13}$C-NMR (100 MHz, acetone-d$_6$) δ: 77.6 (C-2), 68.2-69.3 (C-3), 26.8 (C-4), 100.1 (C-4a), 151.2 (C-5), 103.2-103.8 (C-6,8), 151.2 (C-7), 149.2 (C-8a), 130.9 (B-ring C-1), 106.4 (B-ring C-2,6), 146.3 (B-ring C-3,5), 133.0 (B-ring C-4), 121.7 (galloyl C-1), 110.0 (galloylC-2,6), 145.8 (galloyl C-3,5), 138.7 (galloylC-4), 166.2, 166.3 (galloylC-7). 97.7, 97.9, 98.4 (Acr-C-1,1'), 26.8 (Acr-C-2,2'), 15.5 (Acr-C-3,3'), 174.8 (COOH), 25.6, 26.7, 30.4, 34.2 (CH$_2$, overlapped with solvent signals), 68.2-69.3 (CH$_2$O).

2. Sample Preparation

APP-H4 cells were seeded to a 6-well plate at a density of 12×10$^4$ cells/1.5 mL, and cultured in Dulbecco's modified Eagle's medium (DMEM; Nacalai Tesque, Inc.) added with 10% fetal bovine serum (FBS; Equitech-Bio, Inc. [Kerrville, Tex., USA]), 100 U/mL penicillin+100 µg/mL streptomycin (Nacalai Tesque, Inc.). After culture for 24 hr, the culture supernatant was removed, and the medium was exchanged with a medium with reduced use amount of serum, Opti-MEM (registered trade mark) I Reduced Serum Medium (Life Technologies Corporation, Carlsbad, Calif., USA) (1 mL). A polyphenol derivative (1 µL) to be the test target was added, and the mixture was further cultured for 48 hr. After culture, the culture supernatant was recovered in a tube (total amount 1.5 mL), centrifuged at 4,000×g/4° C./10 min to remove dead cells, and the supernatant (800 µL) was placed in a new tube. The culture supernatant was preserved at −80° C. before sample preparation. The cells were washed twice with ice-cooled phosphate-buffered saline (PBS). Thereafter, the cells were scraped from the plate using a Cell Scraper. The cells were recovered in a 1.5 mL tube and centrifuged at 4,000×g/4° C./10 min. The supernatant was removed and the cells were preserved at −80° C. before sample preparation. The frozen cells were lysed in 40 µL of solubilization buffer containing 1% Triton X-100, protease inhibitor cocktail Complete™ EDTA-free (Roche) and 50 mM Tris-HCl on ice. The cell lysate was incubated on ice for 60 min, centrifuged at 4° C., 21,900×g for 30 min, and the supernatant was recovered and used as a solubilization cell extract.

The total protein concentration of the cell extract was determined by a BCA protein assay kit (Takara) by using BSA as the standard solution. The final concentration of the test compound used was 1 µM or 10 µM, and quantification was performed using each solvent as a control.

3. Measurement of Neprilysin Activity

The neprilysin-dependent neutral endopeptidase activity of the cell extract was measured fluorescence quantitatively by an indirect coupled enzyme assay method. As a neutral endopeptidase substrate, succinyl-Ala-Ala-Phe-7-amino-4-methylcoumarin (suc-AAF-AMC) (1-1315; Bachem) was used. Total 50 µL of the reaction mixture was prepared such that the final concentration was substrate 0.1 mM suc-AAF-AMC, protein in the cell extract 1-6 µg, 100 mM MES buffer (pH 6.5). With the time of addition of the substrate as the start of the reaction, the mixture was reacted at 37° C. for 1 hr, and Phe-AMC was cut out from the substrate by neutral endopeptidase. Then, to the reaction mixture was added a solution (2.5 µL) containing 0.1 mg (0.4 unit equivalent)/mL leucine aminopeptidase (L-5006; Sigma-Aldrich), and 0.2 mM phosphoramidon (4082; Peptide Institute). The mixture was reacted at 37° C. for 30 min, and Phe (phenylalanine) residue was cut out from Phe-AMC by aminopeptidase. Using microplate spectrometer Infinite M-1000 (Tecan), the fluorescence intensity of free AMC was measured by measuring at an excitation wavelength 390 nm and a fluorescence wavelength 460 nm on a half-well size 96-well black plate (#3695; Corning). The neprilysin-dependent neutral endopeptidase activity was determined based on a decrease in the activity due to 10 µM thiorphan (T-6031; Sigma-Aldrich) as a neprilysin specific inhibitor.

4. Measurement of Neprilysin, α-Secretase and β-Secretase Expression Amounts

The aforementioned cell extract was mixed with 6×SDS-polyacrylamide gel electrophoresis (SDS-PAGE) sample buffer (Nacalai Tesque, Inc.) at a ratio of 5:1, boiled for 5 min, and used as a detection sample of neprilysin, α-secretase and β-secretase proteins.

Using a 18-well comb, 7.5% acrylamide gel was produced. The Lapidus Mini-slab electrophoresis tank used for electrophoresis was purchased from Atto Corporation (Tokyo, Japan), and power supply was purchased from GE Healthcare UK Ltd. (Buckinghamshire, England).

SDS-PAGE was performed using the prepared sample by 20 µL. The 50 V constant voltage was used up to the boundary between the concentration gel and the separation gel, after which the voltage was changed to 100 V and electrophoresis was continued until the dye dripped from the glass plate. Polyvinylidene fluoride (PVDF) membrane (GE Healthcare UK Ltd.) was immersed in methanol for 20 seconds, and in a transfer buffer for not less than 30 min to hydrophilize the PVDF membrane. After electrophoresis, the gel was immersed in the transfer buffer and shaken to remove SDS. The hydrophilized PVDF membrane and gel were sandwiched between filter paper impregnated with the transfer buffer and the protein in the gel was transferred to the PVDF membrane in a tank manner (Bio-Rad Laboratories, Inc, Hercules, Calif., USA).

The PVDF membrane after transfer was washed with a wash buffer and immersed in a blocking buffer to prevent non-specific binding of the primary antibody, and a blocking reaction was performed at room temperature for 1 hr. Thereafter, this mixture was reacted with a primary antibody (anti-CD10 mouse IgG monoclonal antibody [clone 56C6, NCL-CD10-270, Leica Biosystems, Ltd] (1 µg/mL), or an anti-human neprilysin polyclonal antibody [AF1182, R&D systems., Inc.] (1 µg/mL); FL-APP, anti-C-terminus region of human APP rabbit polyclonal antibody (A8717, Sigma-Aldrich) (1 µg/mL); ADAM10, anti-ADAM10 antibody, C-terminus (AB19031, Merck Millipore); BACE1, anti-BACE (Ab-2) (485-501) polyclonal antibody (PC529, Calbiochem); β-actin, anti-β-actin mouse monoclonal antibody (clone AC15, A5441, Sigma-Aldrich)) to perform an antigen-antibody-reaction at 4° C. for not less than 16 hr. The PVDF membrane after the reaction was washed with the wash buffer and the secondary antibody (horseradish peroxidase conjugated anti-mouse or anti-rabbit IgG (1:10,000; GE Healthcare UK Ltd.)) corresponding to the primary antibody was reacted at room temperature for 1 hr and detection was carried out using the ECL Select Western Blotting Detection Kit (GE Healthcare UK Ltd.).

The signal intensity of the band was quantified using a densitometer LAS-4000 (GE Healthcare UK Ltd.) and image analysis software Science Laboratory 2003 Image Gauge Version 4.23 (Fujifilm Holdings Corporation, Tokyo, Japan).

5. Measurement of α- and β-Secretase Activities

After thawing from −80° C., the aforementioned culture supernatant was mixed with 6×SDS-polyacrylamide gel electrophoresis (SDS-PAGE) sample buffer (Nacalai Tesque, Inc.) at a ratio of 5:1, boiled for 5 min, and used as a detection sample of APPsα which is a metabolite of APP by α-secretase and APPsβ which is a metabolite of APP by β-secretase in western blot analysis.

Using a 18-well comb, 7.5% acrylamide gel was produced. The Lapidus Mini-slab electrophoresis tank used for electrophoresis was purchased from Atto Corporation (Tokyo, Japan), and power supply was purchased from GE Healthcare UK Ltd. (Buckinghamshire, England).

SDS-PAGE was performed using the prepared sample by 20 µL. The 50 V constant voltage was used up to the boundary between the concentration gel and the separation gel, after which the voltage was changed to 100 V and electrophoresis was continued until the dye dripped from the glass plate. Polyvinylidene fluoride (PVDF) membrane (GE Healthcare UK Ltd.) was immersed in methanol for 20 seconds, and in a transfer buffer for not less than 30 min to hydrophilize the PVDF membrane. After electrophoresis, the gel was immersed in the transfer buffer and shaken to remove SDS. The hydrophilized PVDF membrane and gel were sandwiched between filter paper impregnated with the transfer buffer and the protein in the gel was transferred to the PVDF membrane in a tank manner (Bio-Rad Laboratories, Inc, Hercules, Calif., USA).

The PVDF membrane after transfer was washed with a wash buffer and immersed in a blocking buffer to prevent non-specific binding of the primary antibody, and a blocking reaction was performed at room temperature for 1 hr. Thereafter, it was reacted with a primary antibody (APPsα, anti-human APPsα mouse monoclonal antibody (2B3, Immuno-Biological Laboratories Co., Ltd., Gunma, Japan) (3 µg/mL); APPsβ, anti-APPsβ, rabbit polyclonal antibody, 1 µg/mL) to perform an antigen-antibody-reaction at 4° C. for not less than 16 hr. The PVDF membrane after the reaction was washed with the wash buffer and the secondary antibody (horseradish peroxidase conjugated anti-mouse or anti-rabbit IgG (1:10,000; GE Healthcare UK Ltd.)) corresponding to the primary antibody was reacted at room temperature for 1 hr and detection was carried out using the ECL Select Western Blotting Detection Kit (GE Healthcare UK Ltd.).

The signal intensity of the band was quantified using a densitometer LAS-4000 (GE Healthcare UK Ltd.) and image analysis software Science Laboratory 2003 Image Gauge Version 4.23 (Fujifilm Holdings Corporation, Tokyo, Japan). For production of an antibody (rabbit anti-APPsβ), a rabbit was immunized with a fusion product of the amino acid sequence on the C-terminal side of APPsβ and hapten antigen and purified (Yahata, N., et al., PLoS One. 6(9): e25788. 2011).

6. Measurement of Neprilysin, α-Secretase and β-Secretase mRNA Expression Amounts In the same manner as in the above-mentioned 2, total RNA was prepared using a High Pure RNA Isolation kit (Roche 11828665001) from the cells to be the test target cells, which were treated with each polyphenol derivative and cultured, and subjected to a reverse transcription reaction using PrimeScript RT-PCR kit (TaKaRaRR014A) to give a sample (cDNA) for real-time PCR.

The prepared sample, Premix Ex taq (Perfect Real Time) (TaKaRaRR039A) and a probe, and a primer were mixed in a tube (TaKaRa SC910A), and real-time PCR reaction (initial denaturation: 95° C. 30 sec, PCR reaction: 95° C. 5 sec, 60° C. 20 sec, 40 times) was performed by Smart Cycler II System machine (TaKaRa).

The probe and primer sets are shown in the following Table 2. The 5'-terminus of the probe was modified by a fluorescent substance FAM, and the 3'-terminus was modified by a quencher substance TAMRA, respectively.

(Results)

Figure 2:
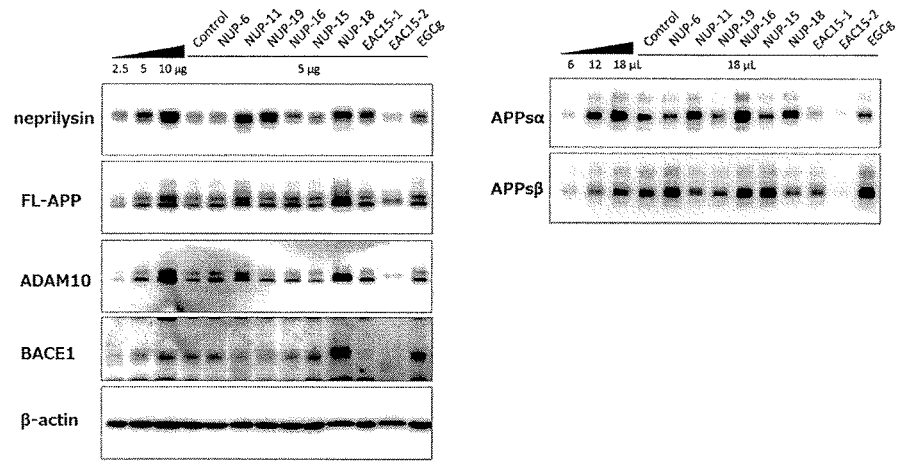
FIG. 2 shows the effect of the polyphenol derivative of the present invention on neprilysin, α-secretase, β-secretase expression levels and APP expression level. The upper Figures show western blot images detected using a specific antibody to neprilysin or each APP, and specific antibodies to ADAM10 and BACE1, and the lower Figures are graphs showing numerical values corresponding thereto, in which the expression level without addition of a polyphenol derivative (Control) is 1. The expression level of β-actin was also measured for standardization.
Figure 2:
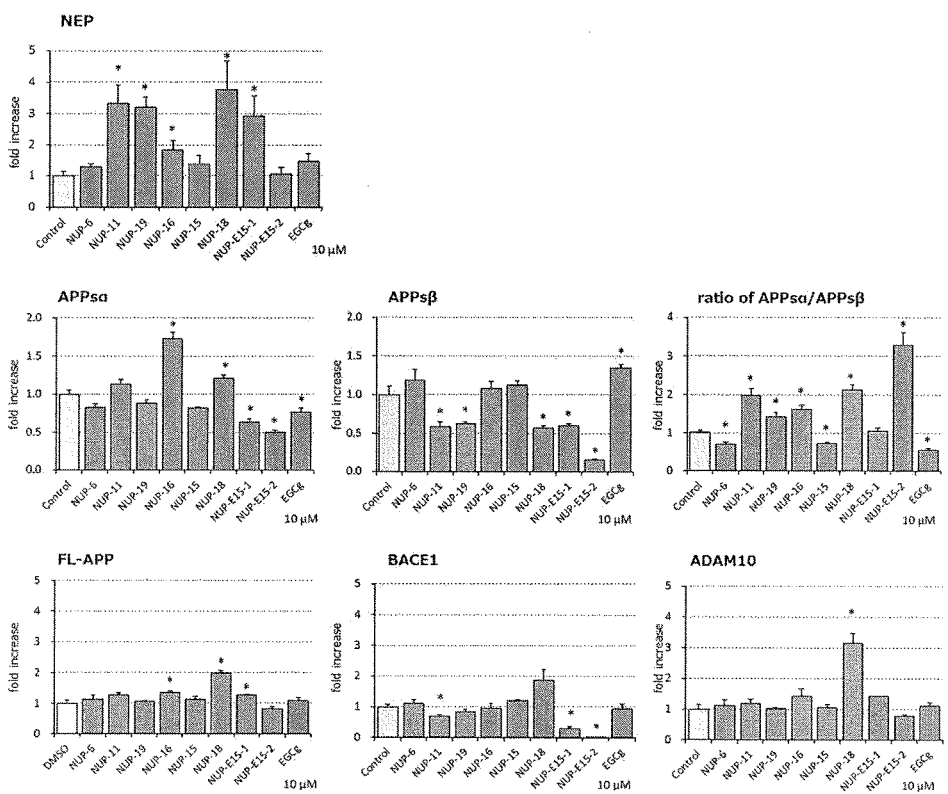
Figure 3:
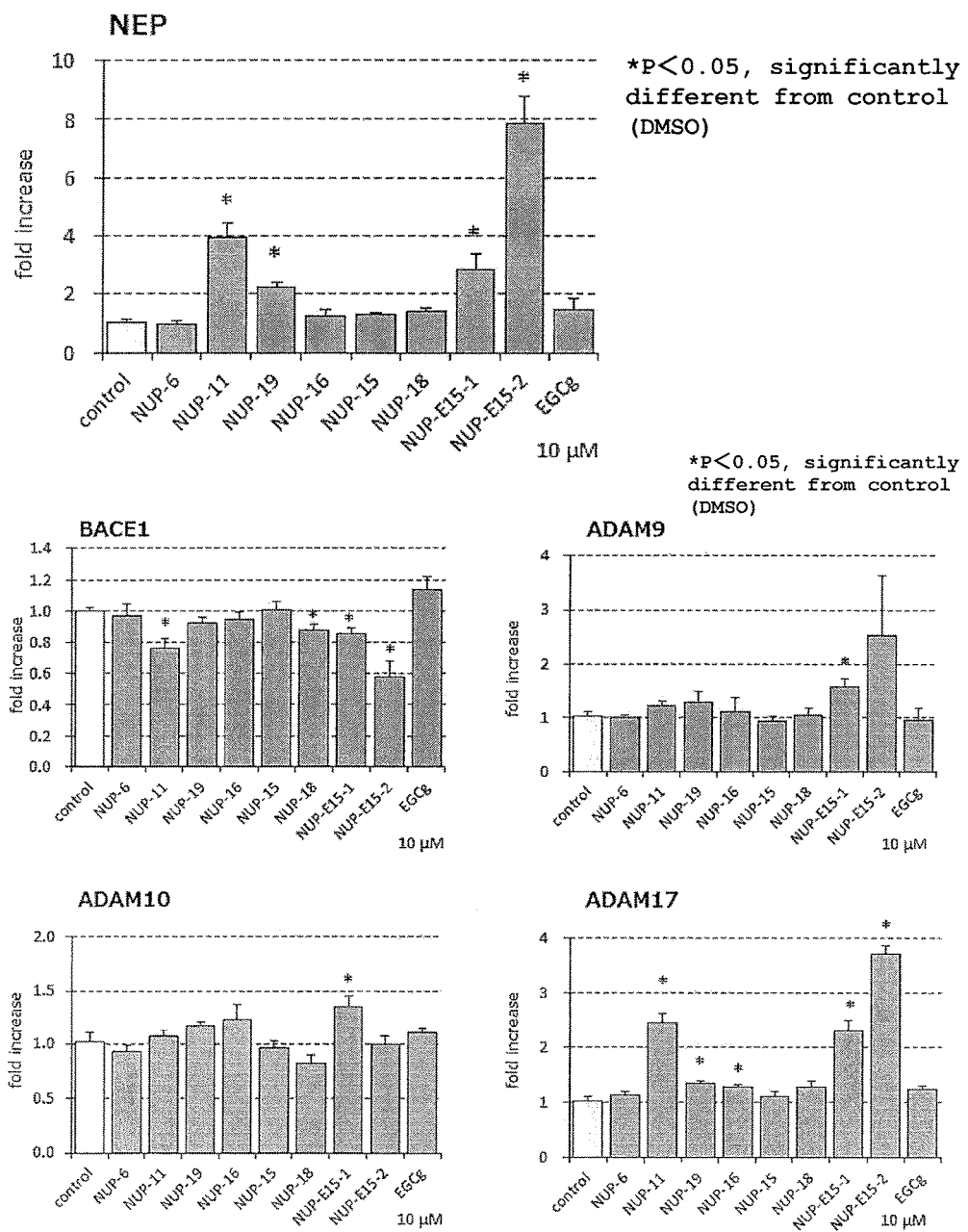
FIG. 3 shows the effect of the polyphenol derivative of the present invention on the expression levels of neprilysin, α-secretase, and β-secretase at mRNA levels. For the measurement, quantitative real-time PCR was performed using the probe and primer set for MME gene for the detection of neprilysin mRNA, respective probes and primer sets for ADAM9, 10 and 17 genes for the detection of α-secretase mRNA, and the probe and primer set for BACE1 gene for the detection of β-secretase mRNA, in which the expression level without addition of a polyphenol derivative (Control) is 1. The expression level of GAPDH mRNA was also measured for standardization.

The neprilysin activity potentiating action by EGCg was about 1.5 times that of control, whereas it was about 3.8 times for NUP-18, about 3.5 times for NUP-11, about 2.7 times for NUP-19, about 1.8 times for NUP-16, about 2.4 times for NUP-E15-1 and about 1.5 for NUP-E15-2 (FIG. 1). The expression amount of neprilysin at the protein level increased to about 3.8 times, about 3.3 times, about 3.2 times, and about 1.8 times that of control for NUP-18, NUP-11, NUP-19, NUP-16, respectively (FIG. 2). The expression level of neprilysin at the mRNA level increased to about 4 times, about 2.1 times, about 2.8 times, and about 7.9 times that of control for NUP-11, NUP-19, NUP-E15-1, and NUP-E15-2, respectively (FIG. 3).

In addition, the neprilysin activity potentiating action of compounds Amentoflavone, Baicalein, Kaempferol, Apigenin, Chrysin and Honokiol, which are polyphenols structurally different from EGCg, was investigated. As a result, it was about 2 times, about 1.7 times, about 1.5 times, about 1.5 times, about 1.4 times, and about 1.3 that of control, respectively (FIG. 1). The neprilysin activity potentiating action of Resveratrol was about 1.4 times that of control.

NUP-16 and NUP-18 potentiate the α-secretase activity to about 1.7 times and about 1.2 times that of control, respectively. NUP-18, NUP-11 and NUP-19 inhibited the β-secretase activity to about 43%, about 41% and about 37% that of control, respectively. The extracellularly secreted APPsα/APPsβ ratio increased to about 2.1 times, about 2.0 times, about 1.6 times, about 1.4 times that of control in NUP-18, NUP-11, NUP-16, NUP-19, respectively (FIG. 2).

At the mRNA level, NUP-E15-1 increased the expression of ADAM9, ADAM10 and ADAM17 to about 1.8 times, about 1.3 times and about 2.2 times, respectively. Regarding ADAM17, the expression increased to about 2.4 times,

TABLE 2

Dual labeled probe & primer design (qPCR)

| Gene | Sequence Name | Sequence | Note |
|---|---|---|---|
| Hs_MME | Hs_MME-Probe | CGGCATGGTCATAGGACACGAAATCACC (SEQ ID No: 3) | |
| | Hs_MME-Forward | GCAGTCCAACTCATTGAACTATGG (SEQ ID No: 4) | |
| | Hs_MME-Reverse | TCTTTGTTAAAGTTTCTGCCATTGT (SEQ ID No: 5) | |
| Hs_ADAM9 | Hs_ADAM9-Probe | TGGACTGGAGATTTGGACCAATGGAAACCT (SEQ ID No: 6) | |
| | Hs_ADAM9-Forward | TGGCAAACTACTTGGATAGTATGTATAT (SEQ ID No: 7) | |
| | Hs_ADAM9-Reverse | CAGCACATCACCAGCACCC (SEQ ID No: 8) | |
| Hs_ADAM10 | Hs_ADAM10-Probe | TCCCTTGCACAGTCTGAATCATCCCGACA (SEQ ID No: 9) | |
| | Hs_ADAM10-Forward | AGTGCAGTCCAAGTCAAGGTC (SEQ ID No: 10) | |
| | Hs_ADAM10-Reverse | GAGCTGTGAAGCCATTACATATTCC (SEQ ID No: 11) | |
| Hs_ADAM17 | Hs_ADAM17-Probe | AGAGCTGACCCAGATCCCATGAAGAACACG (SEQ ID No: 12) | |
| | Hs_ADAM17-Forward | GAACCACCTGAAGAGCTTGTTCA (SEQ ID No: 13) | |
| | Hs_ADAM17-Reverse | GCGATGATCTGCTACCACCAATA (SEQ ID No: 14) | |
| Hs_BACE1 | Hs_BACE1-Probe | TACCAACCAGTCCTTCCGCATCACCATCC (SEQ ID No: 15) | common primers for variants |
| | Hs_BACE1-Forward | GGAACATTTTCCCAGTCATCTCAC (SEQ ID No: 16) | |
| | Hs_BACE1-Reverse | CTGTGAGATGGCAAACTTGTAACA (SEQ ID No: 17) | |
| Hs_GAPDH | Hs_GAPDH-Probe | CCCACTCCTCCACCTTTGACGCTGG (SEQ ID No: 18) | |
| | Hs_GAPDH-Forward | CTCCTCTGACTTCAACAGCGA (SEQ ID No: 19) | |
| | Hs_GAPDH-Reverse | CCAAATTCGTTGTCATACCAGGA (SEQ ID No: 20) | |

7. Statistical Analysis

The numerical values in all experimental data show mean±standard deviation (S.D.). The p value was determined by multiple comparison analysis by Student-Newman-Keuls test using Sigma Plot (Systat Software, Inc., Chicago, Ill., USA) after one-way ANOVA, wherein p<0.05 was taken as significant.

about 1.3 times, about 1.2 times and about 3.7 times that of control for NUP-11, NUP-19, NUP-16, NUP-E15-2, respectively.

From the above results, it is clear that NUP-16 is a double modulator that potentiates the activities of both neprilysin and α-secretase, NUP-11 and NUP-19 are double modulators that potentiate neprilysin activity and inhibit β-secretase activity, and NUP-18, NUP-E15-1 and NUP-E15-2 are triple modulators that potentiate the activities of both neprilysin and α-secretase and inhibit β-secretase.

Example 2

1. Neprilysin Activity Staining of Primary Culture Nerve Cells

This is a method of measuring the amount of neprilysin localized on the cell membrane surface by using cultured cells. Since Aβ is secreted extracellularly, the more neprilysin is present on the cell membrane, the more efficiently Aβ can be degraded and removed. The following procedure was performed according to a previous report (JP-A-2004-151079; Saito T., Iwata N., et al., Nat. Med. 11(4), 434-439, 2005).

Nerve cells prepared from mouse embryocerebral cortex and hippocampus were cultured and fixed, and reacted with a substrate. After completion of the reaction, aminopeptidase-phosphoramidon mixture and nitrosalicylaldehyde solution were sequentially added and reacted. For the cells after completion of the reaction, positively stained images were observed using a filter for argon laser and rhodamine under a confocal laser microscope. More conveniently, it is also possible to observe positively stained images by using a FITC filter under a fluorescence microscope. When the substrate is degraded by neprilysin, an insoluble fluorescence reaction product is formed, and the site where neprilysin is present is visualized in yellow (pseudocolor and could be green). When the cells are stained by this method, the copresence of thiorphan, which is a specific inhibitor of neprilysin, causes disappearance of the positively stained images, and therefore, the presence of neprilysin on the cell surface of primary culture nerve cells of mouse embryocerebral cortex and hippocampus can be confirmed.

2. Induction of Neprilysin Enzyme Activity by Various Compounds

Figure 4:
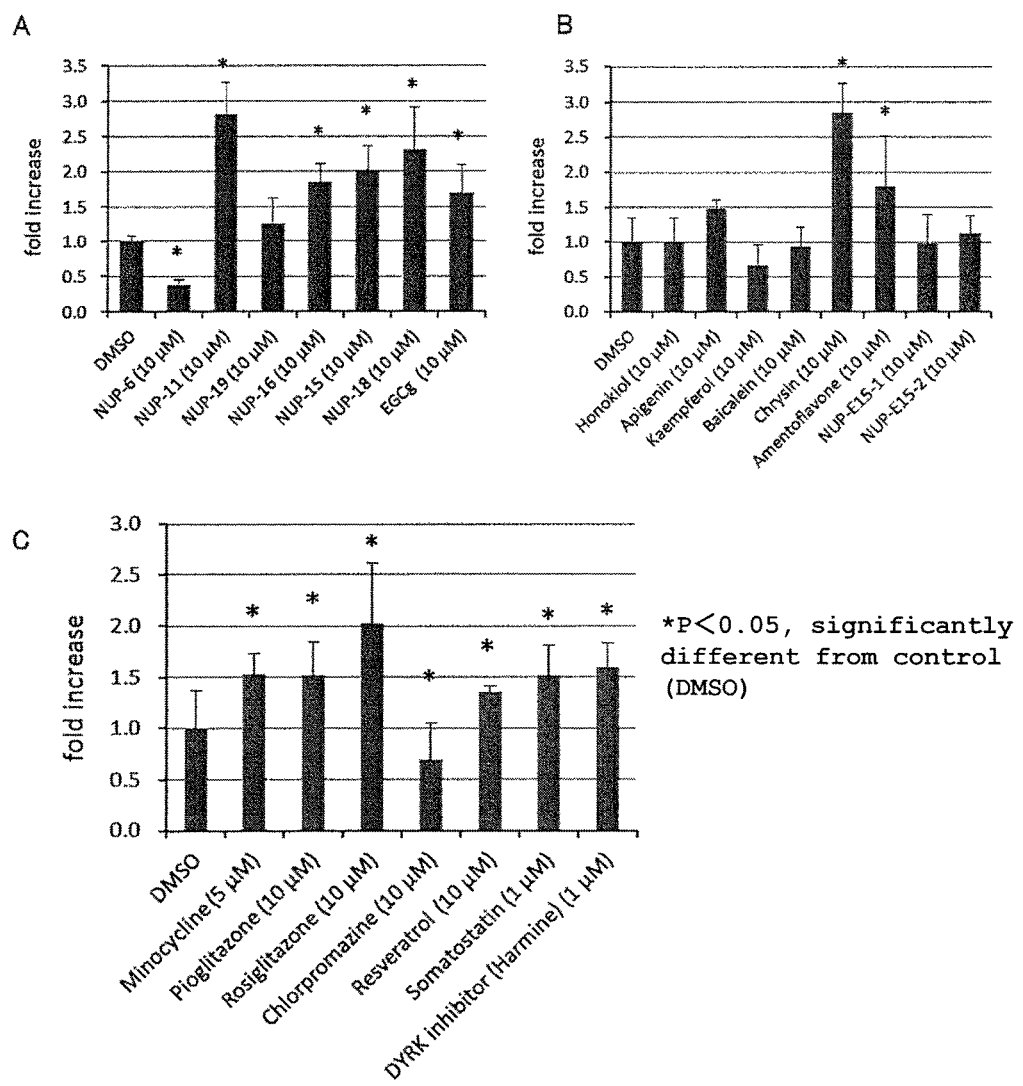
FIG. 4 shows the results of activity staining of neprilysin by using mouse primary cultured cells. A-C show the results of neprilysin activity measured by the activity staining method. The signal intensity without addition of a polyphenol derivative (DMSO) is 1.

The nerve cells prepared from mouse embryocerebral cortex and hippocampus were cultured, the following test compounds were individually added at a given concentration from day 7 to day 21 of culture, and further cultured for 48 hr. After completion of the culture, the neprilysin activity of the mouse primary culture nerve cells was visualized and observed by the method shown in the above-mentioned 1. The stained images were quantified by an image analysis software (MetaMorph, ver. 7.7 (Universal Imaging Corporation, Downington, Pa.)) and studied. With the signal intensity of the cells free of addition (negative control: DMSO) as 1, the results of each test compound were shown in a relative manner. The results are shown in FIG. 4. Somatostatin is known to be an activity regulation molecule of endogenous neprilysin, and was used as a positive control.

(Test Compound)
First Group
NUP-6, NUP-11, NUP-19, NUP-16, NUP-15, NUP-18, EGCg

All compounds were prepared in the same manner as in Example 1 and used for the test at a final concentration of 10 μM. The results are shown in FIG. 4A.

Second Group
Honokiol, Apigenin, Kaempferol, Baicalein, Chrysin, Amentoflavone, NUP-E15-1, NUP-E15-2

All compounds were prepared in the same manner as in Example 1 and used for the test at a final concentration of 10 μM. The results are shown in FIG. 4B.

Third Group
Minocycline (5 μM), Pioglitazone (10 μM), Rosiglitazone (10 μM), Chlorpromazine (10 μM), Resveratrol (10 μM), Somatostatin (1 μM), DYRK1A inhibitor Harmine (1 μM)

All were commercially available products which were dissolved in DMSO and used for the test at a final concentration shown in the parenthesis. The results are shown in FIG. 4C.

3. Results

FIG. 4A-C show the results of neprilysin activity measured by an activity staining method. FIG. 5 schematically shows variation of each factor for polyphenol derivative based on the results of FIGS. 1, 2, 3, 4A-C.

From FIGS. 4A and B, it was found that when treated with the polyphenol derivative of the present invention, the amount of neprilysin transferred to the cell membrane increases, that is, the polyphenol derivative of the present invention promotes the transport of neprilysin to the cell membrane. Since Aβ is extracellularly secreted, the more neprilysin is present on the cell membrane, the more efficiently Aβ can be degraded and removed. Therefore, the polyphenol derivative of the present invention which has an action to promote translocation of neprilysin on the cell surface and acts to efficiently degrade secreted Aβ is useful for the prophylaxis and/or treatment of AD.

From FIG. 4C, it was confirmed that a series of compounds such as Minocycline, Pioglitazone, Rosiglitazone, Chlorpromazine, Resveratrol, Somatostatin, and DYRK1A inhibitor Harmine have a neprilysin activity potentiating action. As an other DYRK1A inhibitor, proINDY is exemplified.

Example 3

Cocktail Therapy by Combined Use of β-Secretase Inhibitor and γ-Secretase Inhibitor As a test compound, the polyphenol derivative of the present invention, NUP-11 (prepared in Example 1; 10 μM) was used. As a BSI, β-secretase inhibitor IV (N-[(1S,2R)-1-benzyl-3-(cyclopropylamino)-2-hydroxypropyl]-5-[methyl(methylsulfonyl)amino-N'-[(1R)-1-phenylethyl] isophthalamide (Merck KGaA; 0.1 μM) was used and, as a GSI, Compound E ((S,S)-2-[2-(3,5-difluorophenyl)-acetylamino]-N-(1-methyl-2-oxo-5-phenyl-2,3-dihydro-1H-benzo[e][1,4]diazepin-3-yl)-propionamide) (Merck KGaA; 0.1 nM) was used. A cocktail therapy was performed using all three kinds of NUP-11 (10 μM), β-secretase inhibitor IV (0.1 μM) and Compound E (0.1 nM).

Figure 6:
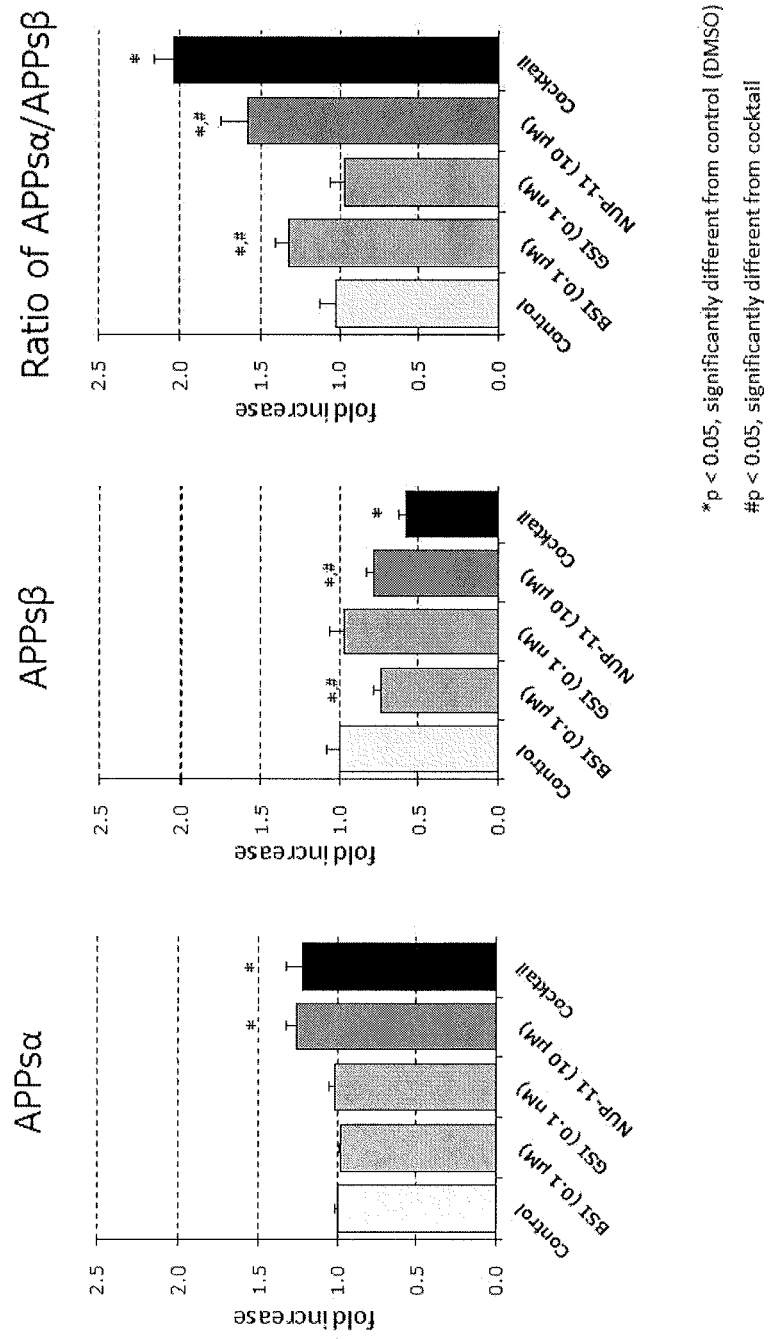
FIG. 6 shows the effects of β-secretase inhibitor (BSI), γ-secretase inhibitor (GSI), the polyphenol derivative of the present invention (NUP-11) and combined use thereof (Cocktail) on the soluble extracellular fragment of APP generated by α-secretase (APPsα) amount, soluble extracellular fragment of APP generated by β-secretase (APPsβ) amount and APPsα/APPsβ (α/β) ratio, in which the expression level without addition of a test compound (Control) is 1.

In the same manner as in Example 1, APPsα production amount, APPsβ production amount and APPsα/APPsβ ratio in the cell extracts of the cells treated with each test compound were measured. As a result, the polyphenol derivative of the present invention used in combination with a low concentration of BSI and GSI and added to the cultured cells increased the APPsα level and decreased the APPsβ level (FIG. 6).

Furthermore, an Aβ production suppressive effect of the cocktail therapy was examined.

In the same manner as in Example 1, a cell extract was prepared using cells simultaneously treated with all three kinds of NUP-11, β-secretase inhibitor IV and Compound E, the Aβ amount of the extract was measured.

Figure 7:
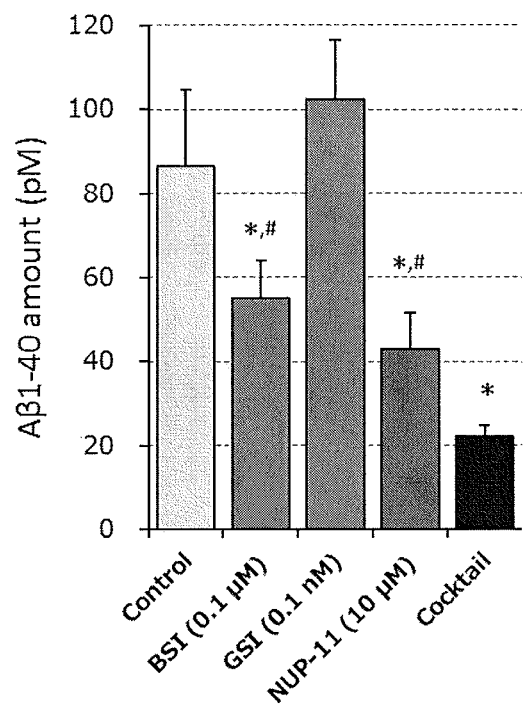
FIG. 7 shows the effects of BSI, GSI, the polyphenol derivative of the present invention (NUP-11) and combined use thereof (Cocktail) on the production amount (pM) of Aβ.

Aβ production was evaluated by measuring the amount of Aβ1-40 BNT77/BA27 monoclonal antibody by using the sandwich ELISA method according to a previous report (Iwata N., et al., J Neurosci 24(4), 991-998, 2004). The results are shown in FIG. 7.

As a result, the cocktail therapy using the polyphenol derivative of the present invention, BSI and GSI was showed a superior Aβ production suppressive action.

Example 4

In Vivo Data by Intracerebral Injection

The polyphenol derivative of the present invention was directly injected intracerebrally, and an influence thereof on the neprilysin activity was examined.

Figure 8:
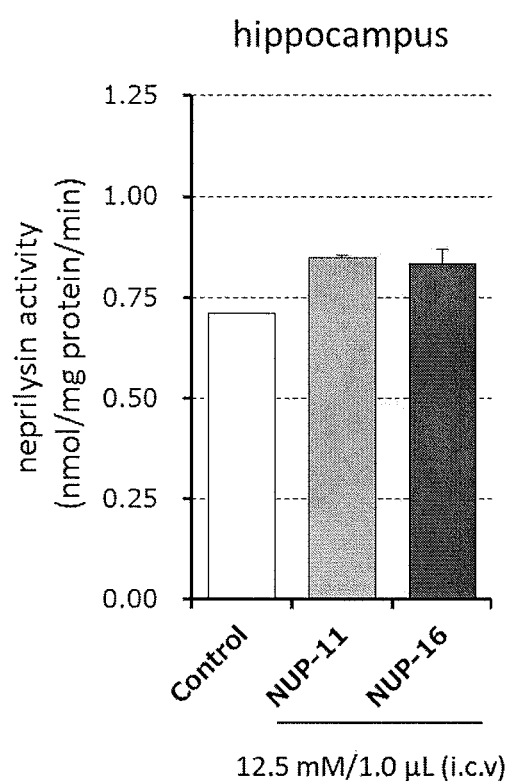
FIG. 8 shows the effect of injection of the polyphenol derivative of the present invention directly into the hippocampus on neprilysin activity. The neprilysin activity is shown as the amount (nmol/mg protein/min) of substrate cleavage per 1 minute per a given protein amount of tissue extract.

According to a previous report (Iwata N., et al., J Neurosci 24(4), 991-998, 2004), the polyphenol derivative of the present invention was intraventricularly administered at a given concentration, a cell extract was prepared from the hippocampus tissue after administration, and evaluated by measuring the neprilysin activity in the same manner as in Example 1. The results are shown in FIG. 8.

As a result, the polyphenol derivative of the present invention showed a superior neprilysin activity potentiating effect also in vivo.

SEQUENCE LISTING FREE TEXT

SEQ ID NO: 1: synthetic substrate
SEQ ID NO: 2: synthetic substrate
SEQ ID NO: 3: Hs_MME-probe
SEQ ID NO: 4: Hs_MME-primer (forward)
SEQ ID NO: 5: Hs_MME-primer (reverse)
SEQ ID NO: 6: Hs_ADAM9-probe
SEQ ID NO: 7: Hs_ADAM9-primer (forward)
SEQ ID NO: 8: Hs_ADAM9-primer (reverse)
SEQ ID NO: 9: Hs_ADAM10-probe
SEQ ID NO: 10: Hs_ADAM10-primer (forward)
SEQ ID NO: 11: Hs_ADAM10-primer (reverse)
SEQ ID NO: 12: Hs_ADAM17-probe
SEQ ID NO: 13: Hs_ADAM17-primer (forward)
SEQ ID NO: 14: Hs_ADAM17-primer (reverse)
SEQ ID NO: 15: Hs_BACE1-probe
SEQ ID NO: 16: Hs_BACE1-primer (forward)
SEQ ID NO: 17: Hs_BACE1-primer (reverse)
SEQ ID NO: 18: Hs_GAPDH-probe
SEQ ID NO: 19: Hs_GAPDH-primer (forward)
SEQ ID NO: 20: Hs_GAPDH-primer (reverse)

INDUSTRIAL APPLICABILITY

As suggested by age-dependent reduction in intracerebral neprilysin level and reduction in neprilysin levels in the AD brain, an increase in the intracerebral Aβ level associated with AD onset process and aging may be caused by decreased neprilysin activity. The present invention can suppress intracerebral Aβ accumulation and prevent the onset of AD or treat AD by inhibiting such decrease in the neprilysin activity (potentiating neprilysin activity).

In addition, the polyphenol derivative of the present invention when added to food or drink is useful as a health food or food for specified health.

This application is based on a patent application Nos. 2014-226236 filed in Japan (filing date: Nov. 6, 2014) and 2015-196282 (filing date: Oct. 1, 2015), the contents of which are incorporated in full herein.

The invention claimed is:

1. A method for the inhibition and/or treatment of Alzheimer's disease, comprising administering an effective amount of a polyphenol derivative to a patient in need thereof, wherein the polyphenol derivative is a compound wherein a liposoluble group is introduced into the (−)-epigallocatechin-3-O-gallate derivative or (−)-epicatechin-3-O-gallate derivative represented by the formula (I):

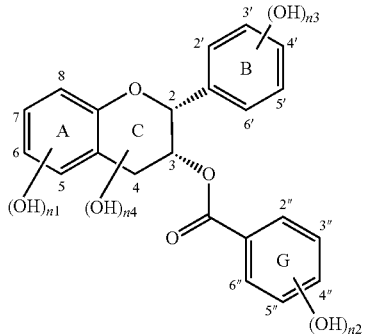

wherein n1 is the number of hydroxyl groups bonded to ring A, and is an integer of 0-4; n2 is the number of hydroxyl groups bonded to ring G, and is an integer of 0-5; n3 is the number of hydroxyl groups bonded to ring B, and is an integer of 0-5; n4 is the number of hydroxyl groups bonded to ring C, and is 0 or 1; and n1+n2+n3+n4 is two or more.

2. The method according to claim 1, wherein the liposoluble group is a chain hydrocarbon group optionally having substituent(s).

3. The method according to claim 1, wherein the liposoluble group is directly introduced into ring A via a C—C bond.

4. The method according to claim 1, wherein the liposoluble group is introduced without using an S-ester bond or O-ester bond.

5. The method according to claim 1, wherein the polyphenol derivative has a coefficient of partition (log P) of not less than 1.8-fold that of (−)-epigallocatechin-3-O-gallate used as a control.

6. The method according to claim 1, wherein the polyphenol derivative is at least one kind selected from the following compound group:

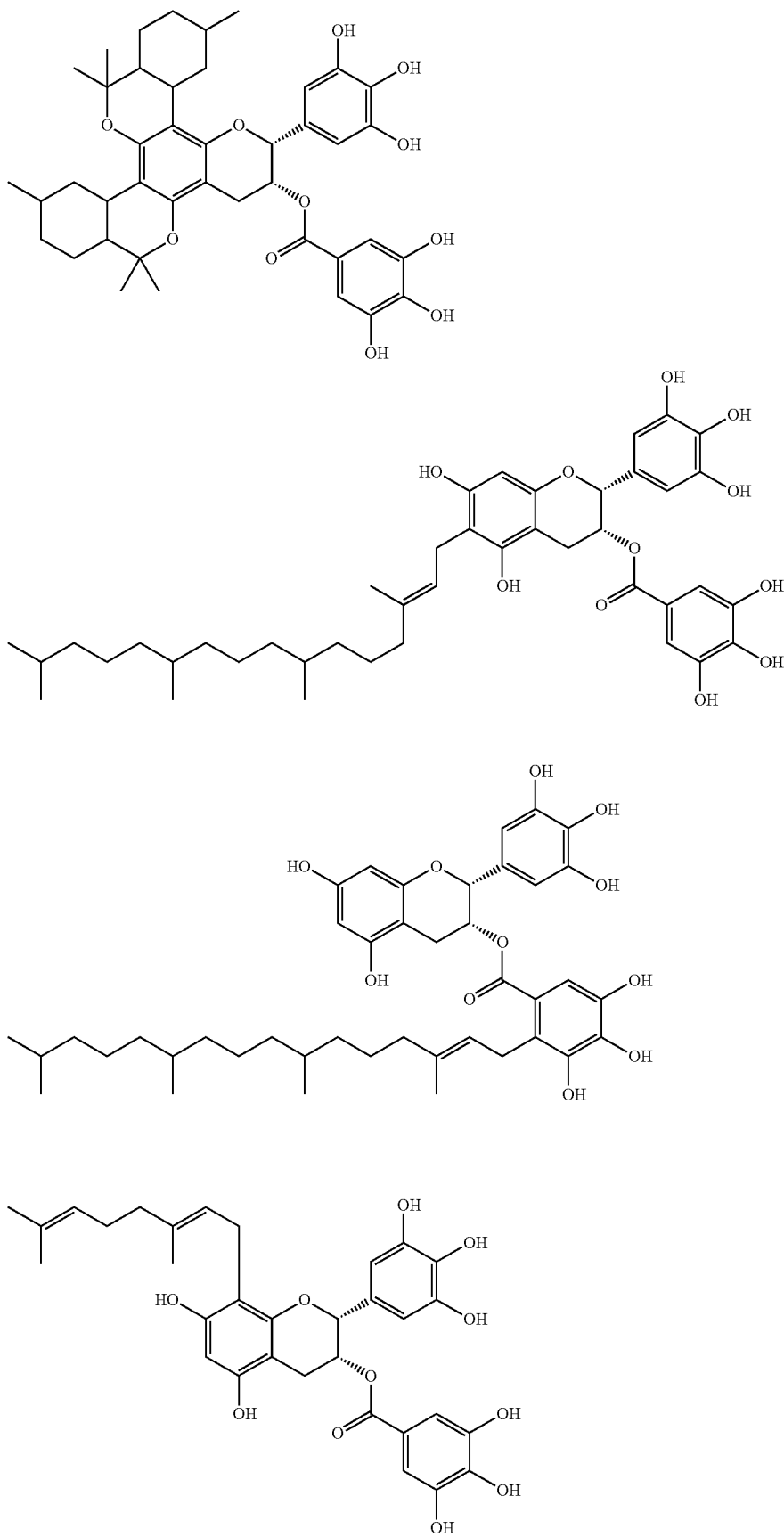

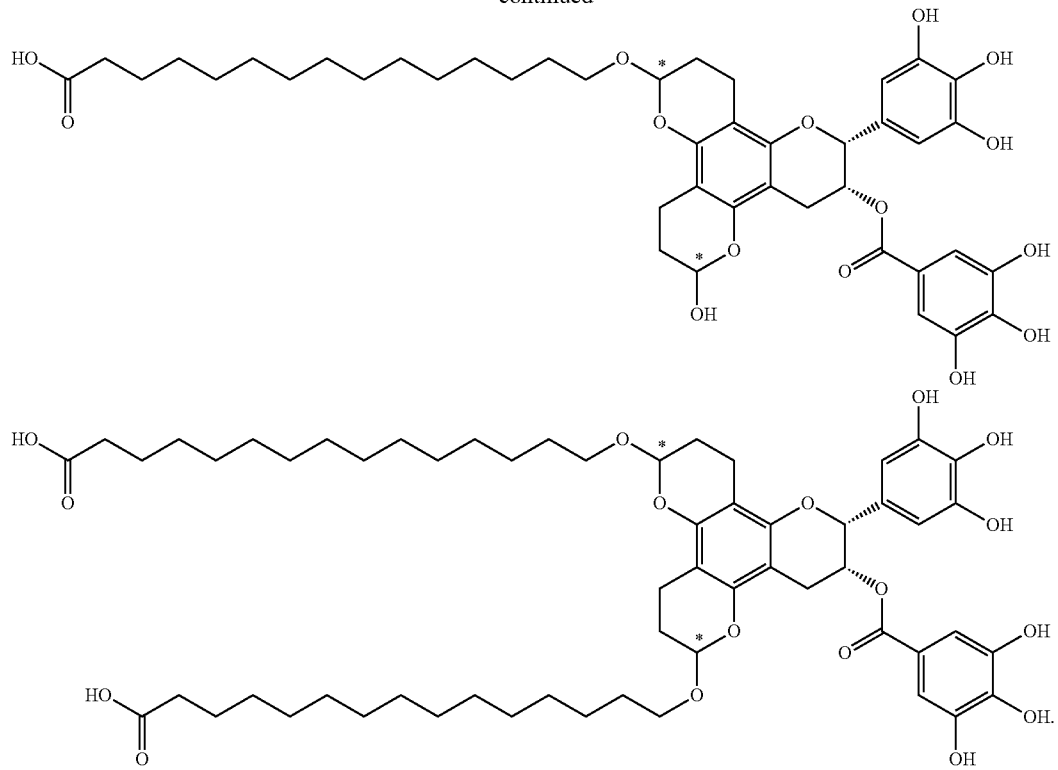

7. The method according to claim 1, wherein the polyphenol derivative is the following compound or derivative thereof:

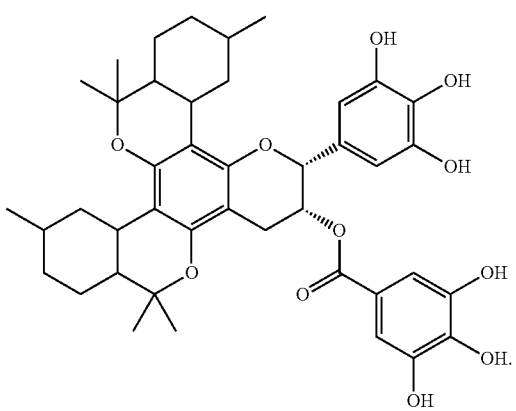 [SMILES: CC1CCC2C(C1)c1c(c3c(c4c1OC(C)(C)C1CCC(C)CC41)O[C@H](c1cc(O)c(O)c(O)c1)[C@H](OC(=O)c1cc(O)c(O)c(O)c1)C3)OC2(C)C]

8. The method according to claim 1, wherein the polyphenol derivative is a catechin derivative or a proanthocyanidin derivative produced by reacting (i) catechin or proanthocyanidin, and (ii) a compound represented by the following formula

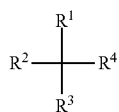

wherein $R^1$ is a hydrocarbon group; $R^2$ is hydrogen or hydrocarbon group; $R^3$ is hydrogen or hydrocarbon group; $R^4$ is a hydroxyl group, or $R^3$ and $R^4$ are joined to show a keto group.

9. The method according to claim 1, wherein the polyphenol derivative is a catechin derivative or a proanthocyanidin derivative produced by reacting (i) catechin or proanthocyanidin, and (ii) 2-hexenal, 2-nonenal, cinnamaldehyde, ferulaldehyde, p-coumaraldehyde, citral, citronellal, geranial, geraniol, farnesal, farnesol, 3,7,11,15-tetramethylhexadecenal, phytol, 3-nonen-2-one or perillaldehyde by adding an acid.

10. A method of potentiating neprilysin activity and α-secretase activity, and/or inhibiting β-secretase activity, comprising administering an effective amount of the polyphenol derivative to a subject in need thereof, wherein the polyphenol derivative is a compound wherein a liposoluble group is introduced into the (−)-epigallocatechin-3-O-gallate derivative or (−)-epicatechin-3-O-gallate derivative represented by the formula (I):

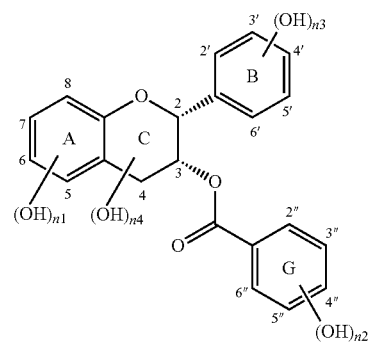

wherein n1 is the number of hydroxyl groups bonded to ring A, and is an integer of 0-4; n2 is the number of hydroxyl groups bonded to ring G, and is an integer of 0-5; n3 is the number of hydroxyl groups bonded to ring B, and is an integer of 0-5; n4 is the number of hydroxyl groups bonded to ring C, and is 0 or 1; and n1+n2+n3+n4 is two or more.

11. The method according to claim 10, wherein the liposoluble group is a chain hydrocarbon group optionally having substituent(s).

12. The method according to claim 10, wherein the liposoluble group is directly introduced into ring A via a C—C bond.

13. The method according to claim 10, wherein the liposoluble group is introduced without using an S-ester bond or O-ester bond.

14. The method according to claim 10, wherein the polyphenol derivative has a coefficient of partition (log P) of not less than 1.8-fold that of (−)-epigallocatechin-3-O-gallate used as a control.

15. The method according to claim 10, wherein the polyphenol derivative is at least one kind selected from the following compound group:

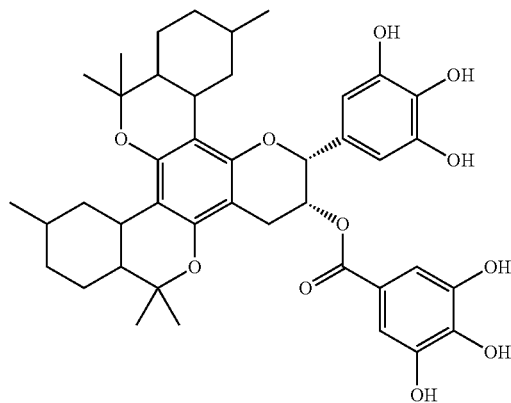

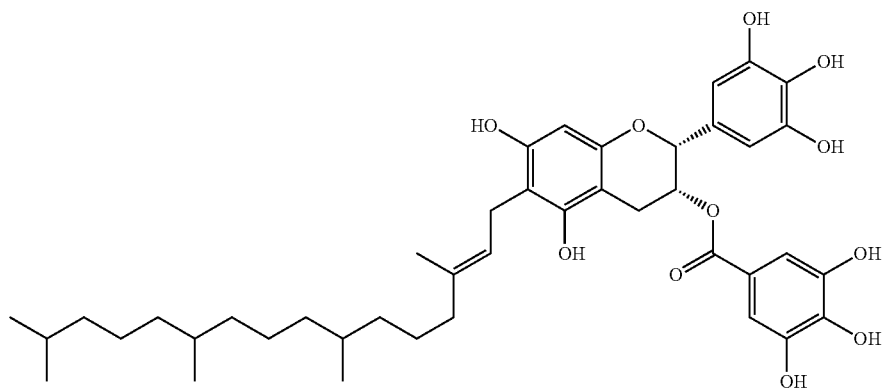

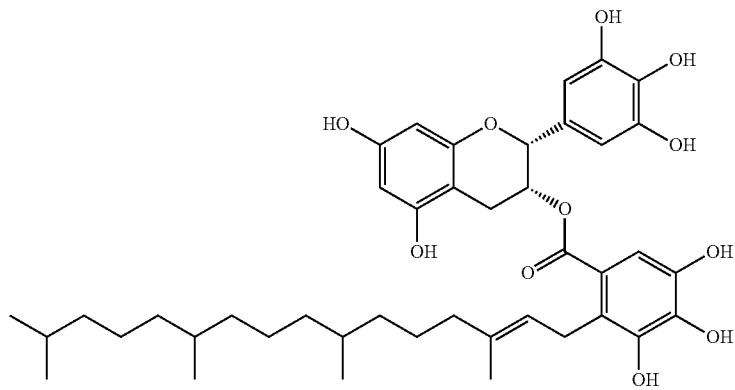

-continued

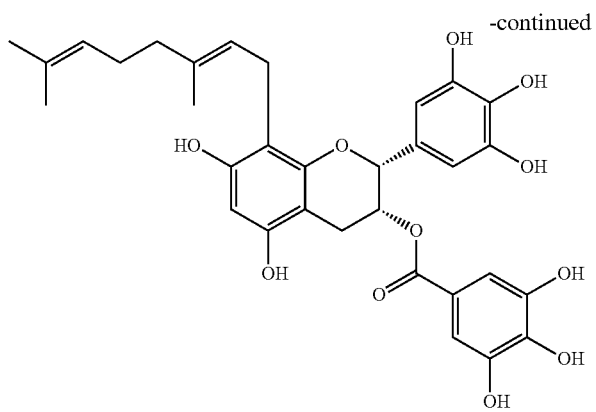

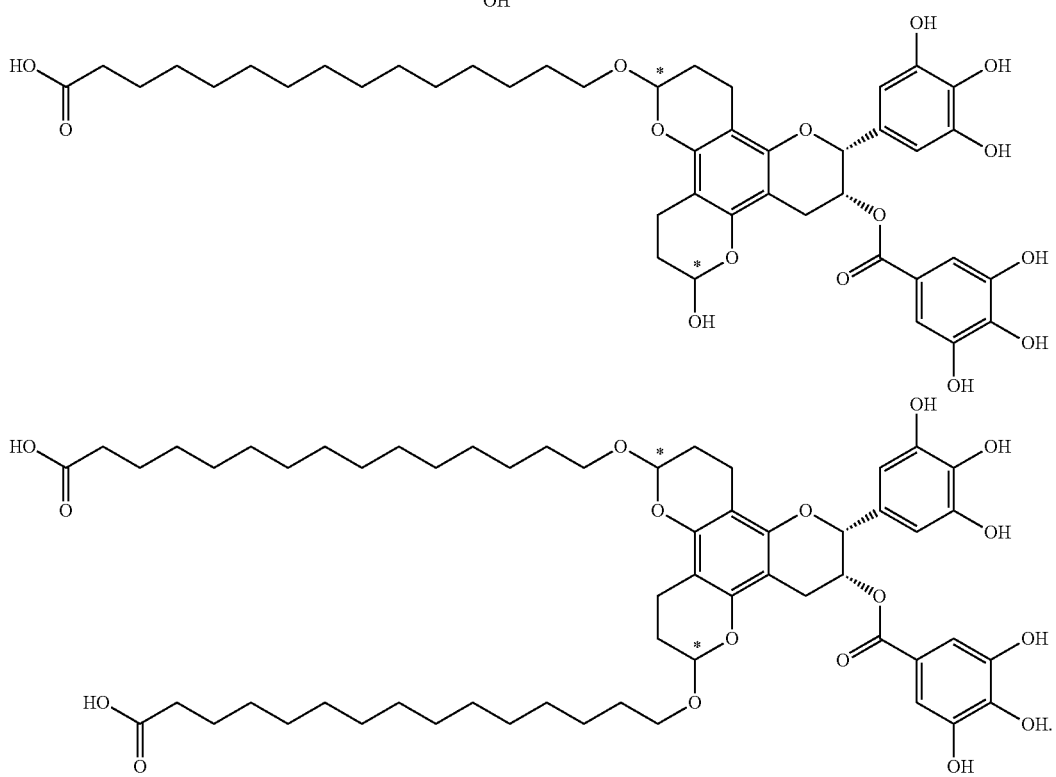

16. The method according to claim 10, wherein the polyphenol derivative is the following compound or derivative thereof:

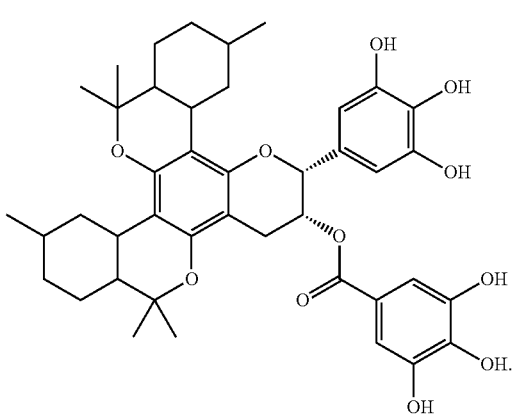 [SMILES: CC1CCC2C(C1)c1c(c3c(c4c1OC(C)(C)C1CCC(C)CC41)O[C@H](c1cc(O)c(O)c(O)c1)[C@H](OC(=O)c1cc(O)c(O)c(O)c1)C3)OC2(C)C]

17. The method according to claim 10, wherein the polyphenol derivative is a catechin derivative or a proanthocyanidin derivative produced by reacting (i) catechin or proanthocyanidin, and (ii) a compound represented by the following formula

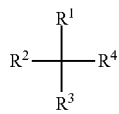

wherein $R^1$ is a hydrocarbon group; $R^2$ is hydrogen or hydrocarbon group; $R^3$ is hydrogen or hydrocarbon group; $R^4$ is a hydroxyl group, or $R^3$ and $R^4$ are joined to show a keto group.

18. The method according to claim 10, wherein the polyphenol derivative is a catechin derivative or a proanthocyanidin derivative produced by reacting (i) catechin or proanthocyanidin, and (ii) 2-hexenal, 2-nonenal, cinnamaldehyde, ferulaldehyde, p-coumaraldehyde, citral, citronellal, geranial, geraniol, farnesal, farnesol, 3,7,11,15-tetramethylhexadecenal, phytol, 3-nonen-2-one or perillaldehyde by adding an acid.

19. A method of potentiating a neprilysin activity, comprising administering an effective amount of a DYRK1A inhibitor to a subject in need thereof.

20. The method according to claim 19, wherein the DYRK1A inhibitor is at least one kind selected from harmine and proINDY.

* * * * *

```
                      SEQUENCE LISTING

<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: synthetic substrate

<400> SEQUENCE: 1

Arg Pro Pro Gly Phe Ser Ala Phe Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Substrate

<400> SEQUENCE: 2

His Gln Lys Leu Val Phe Phe Ala Lys
1               5

<210> SEQ ID NO 3
<211> LENGTH: 28
<212> TYPE: DNA
<213> ORGANISM: Artificial Sequence
<220> FEATURE:
<223> OTHER INFORMATION: Hs_MME-Probe

<400> SEQUENCE: 3
cggcatggtc ataggacacg aaatcacc                                      28
```

<210> SEQ ID NO 4
<211> LENGTH: 24
<212> TYPE: DNA
<213> ORGANISM: Artificial Sequence
<220> FEATURE:
<223> OTHER INFORMATION: Hs_MME-Primer (Forward)

<400> SEQUENCE: 4
gcagtccaac tcattgaact atgg                                          24

<210> SEQ ID NO 5
<211> LENGTH: 25
<212> TYPE: DNA
<213> ORGANISM: Artificial Sequence
<220> FEATURE:
<223> OTHER INFORMATION: Hs_MME-Primer (Reverse)

<400> SEQUENCE: 5
tctttgttaa agtttctgcc attgt                                         25

<210> SEQ ID NO 6
<211> LENGTH: 30
<212> TYPE: DNA
<213> ORGANISM: Artificial Sequence
<220> FEATURE:
<223> OTHER INFORMATION: Hs_ADAM9-Probe

<400> SEQUENCE: 6
tggactggag atttggacca atggaaacct                                    30

<210> SEQ ID NO 7
<211> LENGTH: 28
<212> TYPE: DNA
<213> ORGANISM: Artificial Sequence
<220> FEATURE:
<223> OTHER INFORMATION: Hs_ADAM9-Primer (Forward)

<400> SEQUENCE: 7
tggcaaacta cttggatagt atgtatat                                      28

<210> SEQ ID NO 8
<211> LENGTH: 19
<212> TYPE: DNA
<213> ORGANISM: Artificial Sequence
<220> FEATURE:
<223> OTHER INFORMATION: Hs_ADAMP-Primer (Reverse)

<400> SEQUENCE: 8
cagcacatca ccagcaccc                                                19

<210> SEQ ID NO 9
<211> LENGTH: 29
<212> TYPE: DNA
<213> ORGANISM: Artificial Sequence
<220> FEATURE:
<223> OTHER INFORMATION: Hs_ADAM10-Probe

<400> SEQUENCE: 9
tcccttgcac agtctgaatc atcccgaca                                     29

<210> SEQ ID NO 10
<211> LENGTH: 21
<212> TYPE: DNA
<213> ORGANISM: Artificial Sequence
<220> FEATURE:
<223> OTHER INFORMATION: Hs_ADAM10_Primer (Forward)

<400> SEQUENCE: 10
agtgcagtcc aagtcaaggt c                                         21

<210> SEQ ID NO 11
<211> LENGTH: 25
<212> TYPE: DNA
<213> ORGANISM: Artificial Sequence
<220> FEATURE:
<223> OTHER INFORMATION: Hs_ADAM10-Primer (Reverse)

<400> SEQUENCE: 11
gagctgtgaa gccattacat attcc                                     25

<210> SEQ ID NO 12
<211> LENGTH: 30
<212> TYPE: DNA
<213> ORGANISM: Artificial Sequence
<220> FEATURE:
<223> OTHER INFORMATION: Hs_ADAM17_Probe

<400> SEQUENCE: 12
agagctgacc cagatcccat gaagaacacg                                30

<210> SEQ ID NO 13
<211> LENGTH: 23
<212> TYPE: DNA
<213> ORGANISM: Artificial Sequence
<220> FEATURE:
<223> OTHER INFORMATION: Hs_ADAM17-Primer (Forward)

<400> SEQUENCE: 13
gaaccacctg aagagcttgt tca                                       23

<210> SEQ ID NO 14
<211> LENGTH: 23
<212> TYPE: DNA
<213> ORGANISM: Artificial Sequence
<220> FEATURE:
<223> OTHER INFORMATION: Hs_ADAM17-Primer (Reverse)

<400> SEQUENCE: 14
gcgatgatct gctaccacca ata                                       23

<210> SEQ ID NO 15
<211> LENGTH: 29
<212> TYPE: DNA
<213> ORGANISM: Artificial Sequence
<220> FEATURE:
<223> OTHER INFORMATION: Hs_BACE1-Probe

<400> SEQUENCE: 15
taccaaccag tccttccgca tcaccatcc                                 29

<210> SEQ ID NO 16
<211> LENGTH: 24
<212> TYPE: DNA
<213> ORGANISM: Artificial Sequence
<220> FEATURE:
<223> OTHER INFORMATION: Hs_BACE1-Primer(Forward)

<400> SEQUENCE: 16
ggaacatttt cccagtcatc tcac                                      24

<210> SEQ ID NO 17

```
<211> LENGTH: 24
<212> TYPE: DNA
<213> ORGANISM: Artificial Sequence
<220> FEATURE:
<223> OTHER INFORMATION: Hs_BACE1-Primer (Reverse)

<400> SEQUENCE: 17
ctgtgagatg gcaaacttgt aaca                                              24

<210> SEQ ID NO 18
<211> LENGTH: 25
<212> TYPE: DNA
<213> ORGANISM: Artificial Sequence
<220> FEATURE:
<223> OTHER INFORMATION: Hs_GAPDH-Probe

<400> SEQUENCE: 18
cccactcctc cacctttgac gctgg                                             25

<210> SEQ ID NO 19
<211> LENGTH: 21
<212> TYPE: DNA
<213> ORGANISM: Artificial Sequence
<220> FEATURE:
<223> OTHER INFORMATION: Hs_GAPDH-Primer (Forward)

<400> SEQUENCE: 19
ctcctctgac ttcaacagcg a                                                 21

<210> SEQ ID NO 20
<211> LENGTH: 23
<212> TYPE: DNA
<213> ORGANISM: Artificial Sequence
<220> FEATURE:
<223> OTHER INFORMATION: Hs_GAPDH-Primer (Reverse)

<400> SEQUENCE: 20
ccaaattcgt tgtcatacca gga                                               23
```